United States Patent
Miller et al.

(10) Patent No.: US 11,162,138 B2
(45) Date of Patent: Nov. 2, 2021

(54) MULTI-AMPLITUDE MODULAR LABELED COMPOUNDS

(71) Applicant: Pacific Biosciences of California, Inc., Menlo Park, CA (US)

(72) Inventors: Erik Miller, Berkeley, CA (US); Satwik Kamtekar, Mountain View, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 253 days.

(21) Appl. No.: 16/169,631

(22) Filed: Oct. 24, 2018

(65) Prior Publication Data

US 2019/0127791 A1 May 2, 2019

Related U.S. Application Data

(60) Provisional application No. 62/578,713, filed on Oct. 30, 2017.

(51) Int. Cl.
*G01N 21/64* (2006.01)
*C12Q 1/6869* (2018.01)

(52) U.S. Cl.
CPC ....... *C12Q 1/6869* (2013.01); *G01N 21/6428* (2013.01); *C12Q 2563/131* (2013.01); *G01N 2021/6441* (2013.01)

(58) Field of Classification Search
None
See application file for complete search history.

(56) References Cited

U.S. PATENT DOCUMENTS

| | | |
|---|---|---|
| 5,001,050 A | 3/1991 | Blanco et al. |
| 5,198,543 A | 3/1993 | Blanco et al. |
| 5,576,204 A | 11/1996 | Blanco et al. |
| 5,733,743 A | 3/1998 | Johnson et al. |
| 6,787,308 B2 | 9/2004 | Balasubramanian et al. |
| 6,917,726 B2 | 7/2005 | Levene et al. |
| 7,033,764 B2 | 4/2006 | Korlach et al. |

(Continued)

FOREIGN PATENT DOCUMENTS

| | | |
|---|---|---|
| WO | 2007075987 A2 | 7/2007 |
| WO | 2007076057 A2 | 7/2007 |

(Continued)

OTHER PUBLICATIONS

Alba, "Protein Family Review: Replicative DNA Polymerases" Genome Biology (2001) 2(1):reviews 3002.1-3002.4.

(Continued)

*Primary Examiner* — Robert T. Crow
(74) *Attorney, Agent, or Firm* — Monicia Elrod-Erickson

(57) ABSTRACT

Sets of compounds bearing detectably different groups of labels are provided. Typically, different compounds bear different numbers of a single type of label and are thus distinguishable by the amplitude of signal produced by the label. The compounds are assembled from label components and protein cores to facilitate modular production of the compounds. In compounds containing two or more proteins, the proteins are typically covalently linked. Useful sets of compounds include sets of labeled nucleotide analogs, particularly dye-label nucleotide analogs that include tetravalent biotin-binding protein cores.

18 Claims, 9 Drawing Sheets

Specification includes a Sequence Listing.

(56) References Cited

U.S. PATENT DOCUMENTS

| | | | |
|---|---|---|---|
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,315,019 | B2 | 1/2008 | Turner et al. |
| 7,574,306 | B1 | 8/2009 | Baker et al. |
| 7,692,783 | B2 | 4/2010 | Lundquist et al. |
| 7,715,001 | B2 | 5/2010 | Lundquist et al. |
| 7,901,889 | B2 | 3/2011 | Christians et al. |
| 7,981,632 | B2 | 7/2011 | Schmidt |
| 7,995,202 | B2 | 8/2011 | Lundquist et al. |
| 8,846,881 | B2 | 9/2014 | Korlach et al. |
| 8,927,212 | B2 | 1/2015 | Kong et al. |
| 9,062,091 | B2 | 6/2015 | Bjornson et al. |
| 9,547,003 | B2 | 1/2017 | Howarth |
| 2003/0044781 | A1 | 3/2003 | Korlach et al. |
| 2003/0124576 | A1 | 7/2003 | Kumar et al. |
| 2007/0036511 | A1 | 2/2007 | Lundquist et al. |
| 2007/0105162 | A1* | 5/2007 | Ting ............ C07K 14/465 435/7.5 |
| 2007/0196846 | A1 | 8/2007 | Hanzel et al. |
| 2008/0108082 | A1 | 5/2008 | Rank et al. |
| 2009/0208957 | A1 | 8/2009 | Korlach et al. |
| 2009/0298075 | A1 | 12/2009 | Travers et al. |
| 2010/0075332 | A1 | 3/2010 | Patel et al. |
| 2010/0093555 | A1 | 4/2010 | Bjornson et al. |
| 2010/0112645 | A1 | 5/2010 | Clark et al. |
| 2010/0152424 | A1 | 6/2010 | Korlach et al. |
| 2010/0256342 | A1* | 10/2010 | Salemme ............ B82Y 5/00 530/391.1 |
| 2011/0059505 | A1 | 3/2011 | Hanzel et al. |
| 2011/0189659 | A1 | 8/2011 | Clark et al. |
| 2012/0014837 | A1 | 1/2012 | Fehr et al. |
| 2012/0019828 | A1 | 1/2012 | McCaffrey et al. |
| 2012/0021525 | A1 | 1/2012 | Fehr et al. |
| 2012/0034602 | A1 | 2/2012 | Emig et al. |
| 2012/0052506 | A1 | 3/2012 | Yue et al. |
| 2012/0058469 | A1 | 3/2012 | Shen |
| 2012/0058482 | A1 | 3/2012 | Shen et al. |
| 2012/0077189 | A1 | 3/2012 | Shen et al. |
| 2012/0085894 | A1 | 4/2012 | Zhong et al. |
| 2013/0217007 | A1 | 8/2013 | Kamtekar et al. |
| 2013/0316912 | A1* | 11/2013 | Bjornson ............ G01N 33/582 506/2 |
| 2013/0327644 | A1 | 12/2013 | Turner et al. |
| 2013/0338010 | A1 | 12/2013 | Turner et al. |
| 2014/0051068 | A1 | 2/2014 | Cherf et al. |
| 2014/0094374 | A1 | 4/2014 | Kamtekar et al. |
| 2014/0094375 | A1 | 4/2014 | Kamtekar et al. |
| 2014/0342468 | A1 | 11/2014 | Todd et al. |
| 2015/0065353 | A1 | 3/2015 | Turner et al. |
| 2015/0330987 | A1 | 11/2015 | Bjornson et al. |
| 2016/0083789 | A1 | 3/2016 | Turner et al. |
| 2017/0037462 | A1 | 2/2017 | Turner et al. |
| 2017/0107562 | A1* | 4/2017 | Rothberg ............ C12Q 1/6818 |
| 2017/0145495 | A1 | 5/2017 | Sebo et al. |
| 2017/0145496 | A1 | 5/2017 | Sebo et al. |
| 2017/0145502 | A1 | 5/2017 | Shen et al. |
| 2017/0184580 | A1 | 6/2017 | Shen et al. |
| 2017/0321268 | A1 | 11/2017 | Shen et al. |

FOREIGN PATENT DOCUMENTS

| | | |
|---|---|---|
| WO | 2007123763 A2 | 11/2007 |
| WO | 2008051530 A2 | 5/2008 |
| WO | 2016187580 A1 | 11/2016 |

OTHER PUBLICATIONS

Argaraña, et al., "Molecular Cloning and Nucleotide Sequence of the Streptatividin Gene," Nucleic Acids Res. (1986)14(4): 1871-1882.

Asian, et al., "Engineered Single-Chain Dimeric Streptavidins with an Unexpected Strong Preference for Biotin-4-Fluorescein," J. Proc. Natl. Acad. Sci. USA (2005) 102(24):8507-8512.

Asian, et al., "Engineering a Novel, Stable Dimeric Streptavidin with Lower Isolectric Point," Journal of Biotechnology (2007) 128:213-225.

Baugh, et al., "A Distal Point Mutation in the Streptavidin-Biotin Complex Preserves Structure but Diminishes Binding Affinity: Experimental Evidence of Electronic Polarization Effects?" Biochemistry (2010) 49:4568-4570.

Besanceney-Webler et al., "Increasing the Efficacy of Bioorthogonal Click Reactions for Bioconjugation" Angew. Chem. Int. Ed. (2011) 50:8051-8056.

Brune et al., "Dual Plug-and-Display Synthetic Assembly Using Orthogonal Reactive Proteins for Twin Antigen Immunization" Bioconjugate Chem. (2017) 28:1544-1551.

Burgers et al., "Eukaryotic DNA polymerases: proposal for a revised nomenclature" J Biol Chem. (2001) 276(47):43487-90.

Carne, AF, "Chemical modification of proteins," Methods Mol Biol. 1994; 32:311-20.

Carrico, IS, "Chemoselective modification of proteins: hitting the target," Chem Soc Rev. Jul. 2008; 37(7):1423-31.

Chalker, JM et al., "Chemical modification of proteins at cysteine: opportunities in chemistry and biology," Chem Asian J. May 4, 2009;4(5):630-40.

Demonte et al., "Postsynthetic Domain Assembly with NpuDnaE and SspDnaB Split Inteins" Appl Biochem Biotechnol. (2015) 177(5):1137-51.

DeTitta et al., "Carboxybiotin translocation mechanisms suggested by diffraction studies of biotin and its vitamers" Proc Natl Acad Sci USA. (1980) 77(1):333-7.

DiMarco et al., "Overview of the Main Methods Used to Combine Proteins with Nanosystems: Absorption, Bioconjugation, and Encapsulation," International Journal of Nanomedicine (2010) 5:37-49.

Eid et al., "Real-Time DNA Sequencing From Single Polymerase Molecules," Science (2009) 323:133-138.

Ellman et al., "Biosynthetic method for introducing unnatural amino acids site-specifically into proteins" Methods in Enzymology (1991) 202: 301-336.

Fairhead et al., "SpyAvidin hubs enable precise and ultrastable orthogonal nanoassembly" J. Am. Chem. Soc. (2014) 136: 12355-12363.

Garlick and Giese, "Dissociative binding of alpha- and beta-sulphoxides of biotinylamidoethyl-3-(4-hydroxy-3-[125I]iodophenyl)propionamide to avidin" Biochemical Journal (1990) 268(3):611-613.

Gitlin, et al., "Studies on the Biotin-Binding Site of Streptavidin," Biochem. J. (1988) 256:279-282.

Guimaraes et al., "Site-specific C-terminal and internal loop labeling of proteins using sortase-mediated reactions" Nat Protoc. (2013) 8(9):1787-99.

Hackenberger CP and Schwarzer D., "Chemoselective ligation and modification strategies for peptides and proteins," Angew Chem Int Ed Engl. 2008;47(52):10030-74.

Helpploainen et al., "Rhizavidin from Rhizobiumetli: the First Natural Dimer in the Avidin Protein Family," Biochem. J. (2007) 405: 397-405.

Hendrickson, et al., "Crystal Structure of Core Streptavidin Determined From Multiwavelength Anomalous Diffraction of Synchrotron Radiation," Proc. Natl. Acad. Sci. USA (1989) 86:2190-2194.

Howarth et al., "A Monovalent Streptavidin with Single Femtomolar Biotin Binding Site," Nat Methods (2006) 3: 267-273.

Hübscher et al., "Eukaryotic DNA Polymerases" Annual Review of Biochemistry (2002) vol. 71: 133-163.

Hyster, et al., "Biotinylated Rh(III) Complexes in Engineered Streptavidin for Accelerated Asymmetric C—H Activation," Science (2012) 338:500-503.

Innovative Solutions/Biochemistry Methods and Reagents for Interchim—Multifunctional Cross-linkers. Brochure [online]. Interchim International. Retrieved on Mar. 23, 2017. Retrieved from the internet: http://www.interchim.fr/ft/B/BB033a.pdf.

Iwai et al., "Highly efficient protein trans-splicing by a naturally split DnaE intein from Nostoc punctiforme" FEBS Lett. (2006) 580(7):1853-8.

(56) References Cited

OTHER PUBLICATIONS

Kalia and Raines, "Advances in Bioconjugation" Curr Org Chem. (2010) 14(2): 138-147.

Klumb, et al., "Energetic Roles of Hydrogen Bonds at the Ureido Oyegen Binding Pocket in the Streptavidin-Biotin Complex," Biochemistry (1998) 37(21):7657-63.

Korlach et al., "Long, Processive Enzymatic DNA Synthesis Using 100% Dye-Labeled Terminal Phosphate-Linked Nucleotides," Nucleosides, Nucleotides and Nucleic Acids (2008), 27:1072:1083.

Korlach et al., "Selective Aluminum Passivation for Targeted Immobilization of Single DNA Polymerase Molecules in Zero-Mode Waveguide Nanostructures," PNAS U.S.A. (2008) 105(4): 1176-1181.

Kuhlman et al., "Design of a novel globular protein fold with atomic-level accuracy" Science (2003) 302 (5649):1364-1368.

Kurzban, et al., "The Quaternary Structure of Streptavidin in Urea," J. Biol. Chem. (1991) 266(22):14470-14477.

Levene et al., "Zero-mode Waveguides for Single-molecule Analysis at High Concentration" Science (2003) 299:682-686.

Lundquist et al., "Parallel Confocal Detection of Single Molecules in Real Time," Optics Letters (2008) 33:1026-1028.

Matsumoto et al., "Site-specific tetrameric streptavidin-protein conjugation using sortase A" Journal of Biotechnology (2011) 152:37-42.

Noren et al., "A general method for site-specific incorporation of unnatural amino acids into proteins" Science (1989) 244:182-188.

Sano and Cantor, "Expression of a cloned streptavidin gene in *Escherichia coli*" Proc Natl Acad Sci USA (1990) 87:142-6.

Sano, et al., "Molecular Engineering of Streptavidin," Annals of the New York Academy of Sciences 799 (Enzyme Engineering XIII) (1996) pp. 383-390.

Schmidt, et al., "One-Step Affinity Purification of Bacterially Produced Proteins by Means of the "Strep Tag" and Immobilized Recombinant Core Streptavidin," Journal of Chromatography A (1994) 676:337-345.

Srisawat, et al., "Streptavidin Aptamers: Affinity Tags for the Study of RNAs and Ribonucleoproteins," RNA (2001) 7:632-641.

Stallings and DeTitta, "Crystallographic investigations of biotin and carboxybiotin derivatives" Ann N Y Acad Sci. (1985) 447:152-68.

Steitz, "DNA polymerases: structural diversity and common mechanisms" J Biol Chem (1999) 274:17395-17398.

Tahiri-Alaoui, et al., "High Affinity Nucleic Acid Aptamers for Streptavidin Incorporated into Bi-Specific Capture Ligands," Nucleic Acids Res. (2002) 30(10):e45.

Takakura, et al., "Tamavidins—Novel Avidin-Like Biotin-Binding Proteins from the Tamogitake Mushroom," FEBS Journal: (2009) 276: 1383-1397.

Veggiani et al., "Programmable polyproteams built using twin peptide superglues" Proc Natl Acad Sci USA (2016) 113(5):1202-7.

Vijay-Kumar et al., "Structure of Ubiquitin Refined at 1.8Aresolution," J. Mol. Biol. (1987) 194: 531-544.

Voss, et al., "Mutagenesis of a Flexible Loop in Streptavidin Leads to Higher Affinity for the Strep-Tag II Peptide and Improved Performance in Recombinant Protein Purification," Protein Engineering (1997) 10(8):975-982.

Wilbur, et al., "Streptavidin in Antibody Pretargeting. 4. Site-Directed Mutation Provides Evidence That Both Arginine and Lysine Residues are Involved in Kidney Localization," Bioconjugate Chem. (2004) 15:1454-1463.

Williamson et al., "Efficient N-terminal labeling of proteins by use of sortase" Angew Chem Int Ed Engl. (2012) 51(37):9377-80.

Wilson, et al., "The Use of mRNA Display to Select High-Affinity Protein-Binding Peptides," Proc. Natl. Acad. Sci. USA (2001) 98:3750-3755.

Wormser et al., "Synthesis and Growth-Promoting Activity of dl-cis-Hexahydro-4-( 4-carboxybutyl)-2-cyclopentimidazolone: Carbobiotin" Journal of Pharmaceutical Sciences (1972) 61(7):1168-1170.

Yamakura, F. and Ikeda, K., "Modification of tryptophan and tryptophan residues in proteins by reactive nitrogen species," Nitric Oxide. Mar. 2006; 14(2):152-61.

Zakeri et al., "Peptide tag forming a rapid covalent bond to a protein, through engineering a bacterial adhesin" Proc Natl Acad Sci USA (2012) 109(12):E690-7.

Zettler et al., "The naturally split Npu DnaE intein exhibits an extraordinarily high rate in the protein trans-splicing reaction" FEBS Lett. (2009) 583(5):909-14.

\* cited by examiner

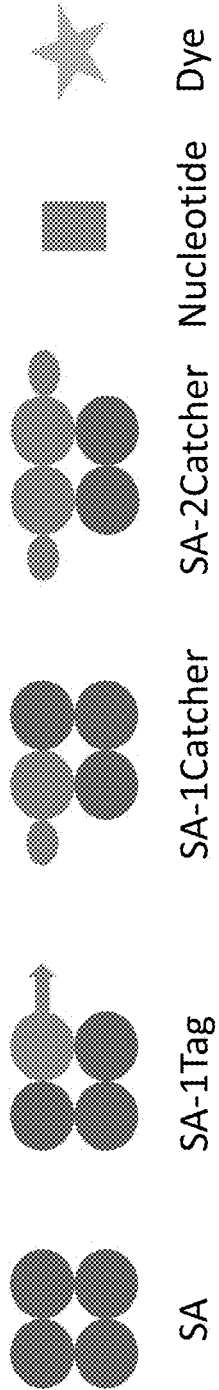
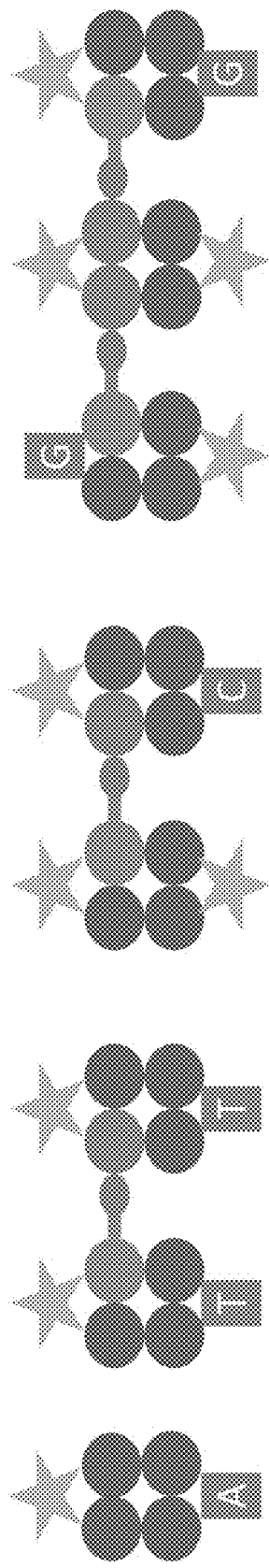
Fig. 1A
Fig. 1B

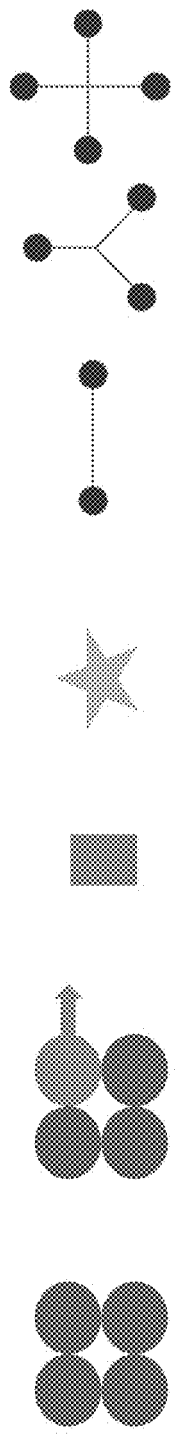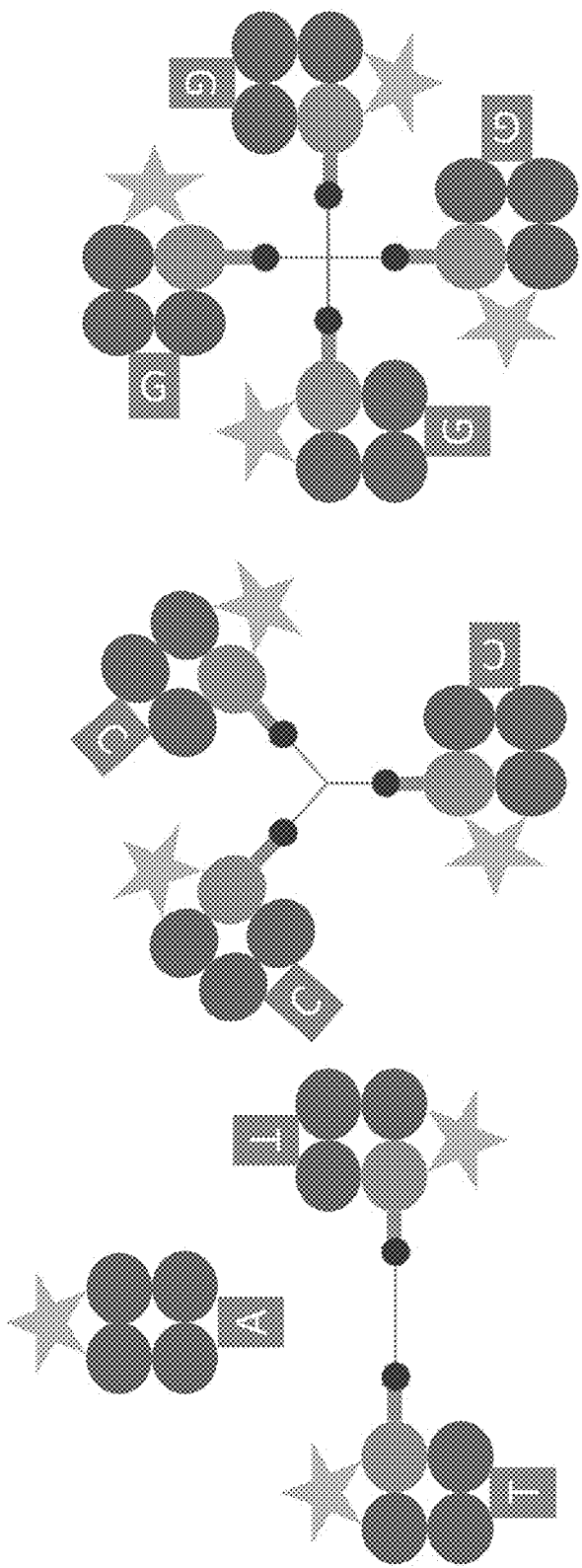
Fig. 4A
Fig. 4B

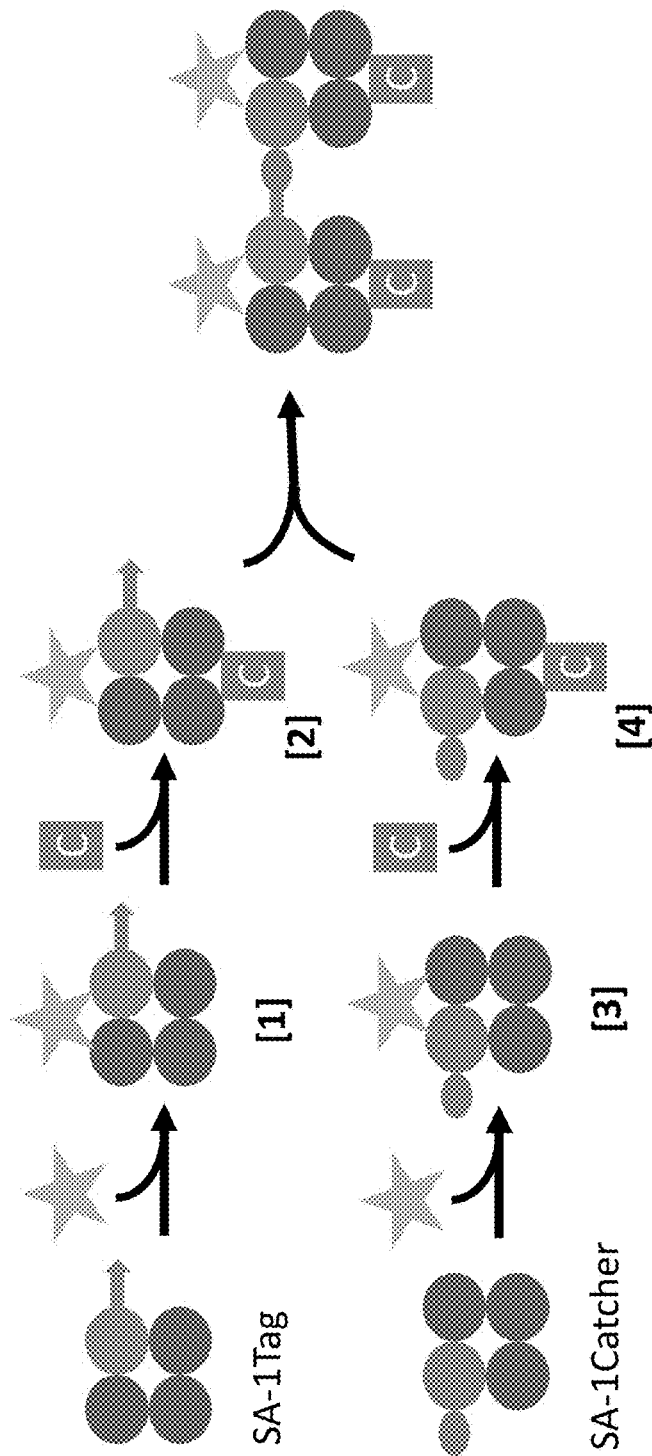
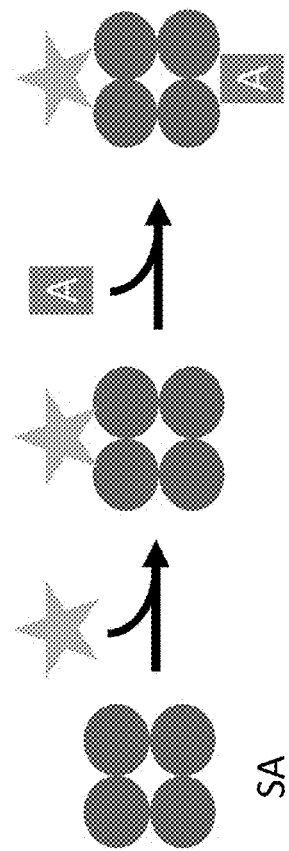
Fig. 7A
Fig. 7B

MULTI-AMPLITUDE MODULAR LABELED COMPOUNDS

CROSS-REFERENCE TO RELATED APPLICATIONS

This application is a non-provisional utility patent application claiming priority to and benefit of prior provisional patent application U.S. Ser. No. 62/578,713, filed Oct. 30, 2017, which is incorporated herein by reference in its entirety for all purposes.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 7 KB file (01020801_2018-12-21_SequenceListing.txt).

STATEMENT REGARDING FEDERALLY SPONSORED RESEARCH

Not applicable.

BACKGROUND OF THE INVENTION

Fluorescence is a primary detection means in numerous areas of molecular biology. Fluorescence is typically a detection means of choice because it is highly sensitive and permits detection of molecules, including single molecules, in a variety of assays, including, e.g., protein analysis and nucleic acid sequencing, amplification and hybridization. Single molecule detection can be performed using pico to nanomolar concentrations of fluorophore for individual molecule detection, or extremely small observation volumes can be used to detect individual molecules up to, e.g., micromolar reagent concentrations. For example, "zero-mode waveguides" (ZMWs), constructed as arrays of subwavelength holes in metal films, can be used to reduce the observation volume of a sample of interest for single molecule detection during processes such as single molecule nucleic acid sequencing. See, e.g., Levene, et al. (2003) Zero-Mode Waveguides for Single Molecule Analysis at High Concentrations" Science 299:682-686.

Different analytes or reagents (e.g., different nucleotide analogs or different antibodies) are typically distinguished from each other through use of different fluorescent labels, typically, different color labels. For some applications, however, labels that can be differentiated by the amplitude rather than the color of their emission are desirable. Modular compounds offering a simple and flexible way to produce multi-amplitude labels are also desirable. The present application provides these and other features that will be apparent upon complete review of the following.

SUMMARY OF THE INVENTION

One general class of embodiments provides a set of dye-labeled nucleotide analogs that includes at least first and second labeled nucleotide analogs. The first labeled nucleotide analog comprises one or more tetravalent biotin-binding proteins, one or more first nucleotide components bound to the tetravalent biotin-binding proteins, and one or more dye components bound to the tetravalent biotin-binding proteins. Each dye component comprises one or more dye moieties. The second labeled nucleotide analog comprises two or more covalently linked tetravalent biotin-binding proteins, one or more second nucleotide components bound to the tetravalent biotin-binding proteins, and two or more dye components bound to the tetravalent biotin-binding proteins. Each dye component in the first and second analogs comprises one or more dye moieties. The total number of dye moieties in the second labeled nucleotide analog is greater than that in the first labeled nucleotide analog.

In some embodiments, each component is bound to the tetravalent biotin-binding protein through a biotin moiety. For example, each component can comprise a bis-biotin moiety that is bound to two biotin binding sites on the tetravalent biotin-binding protein.

The set optionally includes additional analogs. Thus, in one class of embodiments, the set includes a third labeled nucleotide analog that comprises two or more covalently linked tetravalent biotin-binding proteins, one or more third nucleotide components bound to the tetravalent biotin-binding proteins, and three or more dye components bound to the tetravalent biotin-binding proteins. Each dye component comprises one or more dye moieties, and the total number of dye moieties in the third labeled nucleotide analog is greater than that in the second labeled nucleotide analog. In one class of embodiments, the set includes a fourth labeled nucleotide analog comprising three or more covalently linked tetravalent biotin-binding proteins, one or more fourth nucleotide components bound to the tetravalent biotin-binding proteins, and four or more dye components bound to the tetravalent biotin-binding proteins. Each dye component comprises one or more dye moieties, and the total number of dye moieties in the fourth labeled nucleotide analog is greater than that in the third labeled nucleotide analog. In an exemplary class of embodiments, the first labeled nucleotide analog comprises one dye component, the second labeled nucleotide analog comprises two dye components, the third labeled nucleotide analog comprises three dye components, and the fourth labeled nucleotide analog comprises four dye components. Optionally, each dye component comprises a single, identical dye moiety. In some embodiments, the first labeled nucleotide analog comprises one tetravalent biotin-binding protein and one first nucleotide component, the second labeled nucleotide analog comprises two tetravalent biotin-binding proteins and two second nucleotide components, the third labeled nucleotide analog comprises two tetravalent biotin-binding proteins and one third nucleotide component, and the fourth labeled nucleotide analog comprises three tetravalent biotin-binding proteins and two fourth nucleotide components.

The dye components and nucleotide components can be attached to the proteins in essentially any convenient arrangement. For example, where the second labeled nucleotide analog comprises two tetravalent biotin-binding proteins, two nucleotide components, and two dye components, the two nucleotide components can be bound to one of the tetravalent biotin-binding proteins and the two dye components to the other tetravalent biotin-binding protein, or one of the nucleotide components and one of the dye components can be bound to one of the proteins while the other nucleotide component and the other dye component are bound to the other protein.

The dye moieties can be identical or they can be different. Similarly, the dye components in the first and second labeled nucleotide analogs can be identical or they can be different. In some embodiments, the dye moieties are fluorescent dye moieties.

In one class of embodiments, the first nucleotide component comprises at least one phospholinked first nucleotide moiety, the second nucleotide component comprises at least one phospholinked second nucleotide moiety, and the first and second nucleotide moieties comprise different nucleobases. In some embodiments, four analogs are provided, each corresponding to a different nucleobase.

The first labeled nucleotide analog optionally includes two or more tetravalent biotin-binding proteins, e.g., two or more covalently linked tetravalent biotin-binding proteins. In one exemplary class of embodiments, the first labeled nucleotide analog comprises two or more covalently linked tetravalent biotin-binding proteins and two or more first nucleotide components bound to the tetravalent biotin-binding proteins.

A variety of tetravalent biotin-binding proteins are known in the art and are suitable for use in the analogs. In some embodiments, the tetravalent biotin-binding protein comprises streptavidin, avidin, or traptavidin.

In one class of embodiments, the second labeled nucleotide analog comprises two or more tetravalent biotin-binding proteins covalently linked by at least one isopeptide bond. For example, the second labeled nucleotide analog can include two tetravalent biotin-binding proteins covalently linked by an isopeptide bond. In one class of embodiments, the second labeled nucleotide analog comprises two or more tetravalent biotin-binding proteins covalently linked through at least one bifunctional or multifunctional crosslinker. For example, the second labeled nucleotide analog can include two tetravalent biotin-binding proteins covalently linked through a bifunctional crosslinker.

Another general class of embodiments provides a set of dye-labeled nucleotide analogs that includes a first labeled nucleotide analog comprising one or more proteins, one or more first nucleotide components bound to the proteins, and one or more dye components bound to the proteins, each dye component comprising one or more dye moieties; and a second labeled nucleotide analog comprising two or more covalently linked proteins, one or more second nucleotide components bound to the proteins, and two or more dye components bound to the proteins, each dye component comprising one or more dye moieties. The total number of dye moieties in the second labeled nucleotide analog is greater than that in the first labeled nucleotide analog.

A variety of suitable proteins are described herein. In one class of embodiments, the proteins are biotin-binding proteins, and each component is optionally bound to the biotin-binding protein through a biotin moiety (e.g., a bis-biotin moiety). The proteins can be tetrameric biotin-binding proteins or dimeric biotin-binding proteins.

The set optionally includes additional analogs. Thus, in one class of embodiments, the set includes a third labeled nucleotide analog comprising two or more covalently linked proteins, one or more third nucleotide components bound to the proteins, and three or more dye components bound to the proteins, each dye component comprising one or more dye moieties. The total number of dye moieties in the third labeled nucleotide analog is greater than that in the second labeled nucleotide analog. In some embodiments, the set includes a fourth labeled nucleotide analog comprising three or more covalently linked proteins, one or more fourth nucleotide components bound to the proteins, and four or more dye components bound to the proteins, each dye component comprising one or more dye moieties. The total number of dye moieties in the fourth labeled nucleotide analog is greater than that in the third labeled nucleotide analog. In an exemplary class of embodiments, the first labeled nucleotide analog comprises one dye component, the second labeled nucleotide analog comprises two dye components, the third labeled nucleotide analog comprises three dye components, and the fourth labeled nucleotide analog comprises four dye components. Optionally, each dye component comprises a single, identical dye moiety. In some embodiments, the first labeled nucleotide analog comprises one protein and one first nucleotide component, the second labeled nucleotide analog comprises two proteins and two second nucleotide components, the third labeled nucleotide analog comprises two proteins and one third nucleotide component, and the fourth labeled nucleotide analog comprises three proteins and two fourth nucleotide components.

The dye components and nucleotide components can be attached to the proteins in essentially any convenient arrangement. For example, where the second labeled nucleotide analog comprises two proteins, two nucleotide components, and two dye components, the two nucleotide components can be bound to one of the proteins and the two dye components to the other protein, or one of the nucleotide components and one of the dye components can be bound to one of the proteins while the other nucleotide component and the other dye component are bound to the other protein. The dye components and nucleotide components can be covalently or noncovalently bound to the proteins.

The dye moieties can be identical or they can be different. Similarly, the dye components in the first and second labeled nucleotide analogs can be identical or they can be different. In some embodiments, the dye moieties are fluorescent dye moieties.

In one class of embodiments, the first nucleotide component comprises at least one phospholinked first nucleotide moiety, the second nucleotide component comprises at least one phospholinked second nucleotide moiety, and the first and second nucleotide moieties comprise different nucleobases. In some embodiments, four analogs are provided, each corresponding to a different nucleobase.

The first labeled nucleotide analog optionally includes two or more proteins, e.g., two or more covalently linked proteins. In one exemplary class of embodiments, the first labeled nucleotide analog comprises two or more covalently linked proteins and two or more first nucleotide components bound to the proteins.

In one class of embodiments, the second labeled nucleotide analog comprises two or more proteins covalently linked by at least one isopeptide bond. For example, the second labeled nucleotide analog can include two proteins covalently linked by an isopeptide bond. In one class of embodiments, the second labeled nucleotide analog comprises two or more proteins covalently linked through at least one bifunctional or multifunctional crosslinker. For example, the second labeled nucleotide analog can include two proteins covalently linked through a bifunctional crosslinker.

In some aspects, the invention provides a reaction mixture for sequencing a nucleic acid template. The mixture comprises a polymerase enzyme complex comprising a polymerase enzyme, a template nucleic acid, and optionally a primer hybridized to the template nucleic acid, wherein the polymerase enzyme complex is immobilized on a surface, and sequencing reagents in contact with the surface, comprising reagents for carrying out nucleic acid synthesis including a set of dye-labeled nucleotide analogs as described herein.

In some aspects, the invention provides a method for sequencing a nucleic acid template, the method comprising providing a polymerase enzyme complex comprising a polymerase enzyme, a template nucleic acid, and optionally a primer hybridized to the template nucleic acid, wherein the polymerase enzyme complex is immobilized on a surface; adding sequencing reagents in contact with the surface comprising reagents for carrying out nucleic acid synthesis including a set of dye-labeled nucleotide analogs as described herein; and determining the sequential addition of nucleotides to a nucleic acid strand complementary to a strand of the template nucleic acid by observing the interaction of the labeled nucleotide analogs with the polymerase enzyme complex.

In some aspects, the invention provides a system for sequencing nucleic acids, the system comprising a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid, and sequencing reagents in contact with the chip's surface comprising reagents for carrying out nucleic acid synthesis including the set of dye-labeled nucleotide analogs as described herein; an illumination system for illuminating the polymerase enzyme complexes; an optical detection system for detecting fluorescence from the labeled nucleotide analogs while they are interacting with the polymerase enzyme complexes; and a computer for analyzing the signals detected by the detection system to determine the sequential addition of nucleotides to a nucleic acid strand complementary to a strand of the template nucleic acid.

One general class of embodiments provides a composition that includes a first compound comprising one or more proteins and one or more label components bound to the proteins, each label component comprising one or more labels; and a second compound comprising two or more covalently linked proteins and two or more label components bound to the proteins, each label component comprising one or more labels. The total number of labels in the second compound is greater than that in the first compound. The label components on the first and second compounds are optionally identical. Optionally, the labels are all identical.

In some embodiments, the label components are noncovalently bound to the proteins. In one class of embodiments, the proteins are tetrameric biotin-binding proteins, and each label component is optionally bound to the tetrameric biotin-binding protein through a biotin moiety. For example, the tetrameric biotin-binding proteins can be tetravalent biotin-binding proteins, and each label component can comprise a bis-biotin moiety bound to two biotin binding sites on one of the tetravalent biotin-binding proteins. A variety of tetravalent biotin-binding proteins are known in the art and are suitable for use in the compounds. In some embodiments, the tetravalent biotin-binding protein comprises streptavidin, avidin, or traptavidin. In one class of embodiments, the proteins are divalent biotin-binding proteins.

The composition optionally includes additional compounds. Thus, in one class of embodiments, the composition comprises a third compound comprising two or more covalently linked proteins and three or more label components bound to the proteins, each label component comprising one or more labels. The total number of labels in the third compound is greater than that in the second compound. In one class of embodiments, the composition includes a fourth compound comprising three or more covalently linked proteins and four or more label components bound to the proteins, each label component comprising one or more labels. The total number of labels in the fourth compound is greater than that in the third compound. In an exemplary class of embodiments, the first compound comprises one label component, the second compound comprises two label components, the third compound comprises three label components, and the fourth compound comprises four label components. Optionally, each label component comprises a single, identical label. In some embodiments, the first compound comprises one protein and one label component, the second compound comprises two covalently linked proteins and two label components, the third compound comprises two covalently linked proteins and three label components, and the fourth compound comprises three covalently linked proteins and four label components. The label components on the first, second, third, and fourth compounds are optionally identical.

A variety of labels are known in the art and are suitable for use in the compounds. In some embodiments, the labels are optical labels, e.g., fluorescent dye moieties.

In one class of embodiments, the second compound comprises two or more proteins covalently linked by at least one isopeptide bond. For example, the second compound can include two proteins covalently linked by an isopeptide bond. In one class of embodiments, the second compound comprises two or more proteins covalently linked through at least one bifunctional or multifunctional crosslinker. For example, the second compound can include two proteins covalently linked through a bifunctional crosslinker.

In one class of embodiments, the first compound is bound to at least one first molecule of interest, and the second compound is bound to at least one second molecule of interest. For example, the first molecule of interest can be a first antibody specific for a first epitope, and the second molecule of interest can be second antibody specific for a second epitope. Typically, the first and second epitopes are different. As another example, the first molecule of interest can be a first nucleotide while the second molecule of interest is a second nucleotide, typically different from the first.

Compounds can be covalently or noncovalently bound to the molecules of interest. In one exemplary class of embodiments, the proteins are tetravalent biotin-binding proteins, and each molecule of interest comprises a bis-biotin moiety bound to two biotin binding sites on one of the tetravalent biotin-binding proteins.

Where a compound includes two or more proteins, the label components and molecules of interest can be attached to the proteins in essentially any convenient arrangement. For example, where a compound comprises two proteins, two molecules of interest, and two label components, the two molecules of interest can be bound to one of the proteins and the two label components to the other protein, or one of the molecules of interest and one of the label components can be bound to one of the proteins while the other molecule of interest and the other label component are bound to the other protein.

The first compound optionally includes two or more proteins, e.g., two or more covalently linked proteins. In one exemplary class of embodiments, the first compound comprises two or more covalently linked proteins and two or more first molecules of interest bound to the proteins.

BRIEF DESCRIPTION OF THE DRAWINGS

FIG. 1A illustrates exemplary components used to assemble modular analogs. FIG. 1B illustrates an exemplary set of modular, multi-amplitude nucleotide analogs distinguishable by the amplitude of signal from a single type of fluorescent dye.

FIG. 4A illustrates exemplary components used to assemble modular analogs including bifunctional and multifunctional crosslinkers. FIG. 4B illustrates an exemplary set of modular, multi-amplitude nucleotide analogs distinguishable by the amplitude of signal from a single type of fluorescent dye.

FIGS. 7A-7B schematically illustrate production of a pair of modular multi-amplitude nucleotide analogs.

Figure 2A:
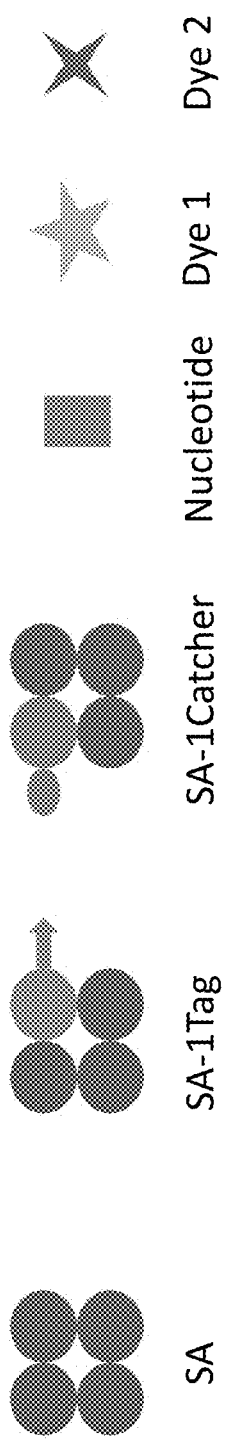
FIG. 2A illustrates exemplary components used to assemble modular analogs.

Schematic figures are not necessarily to scale.

Definitions

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

A "bis-biotin moiety" is a moiety that includes two covalently-linked biotin moieties. For example, a bis-biotin moiety can include two biotins joined by a linker.

The term "linker" or "cross-linker" refers to a molecule or group that connects at least two molecules or groups, typically covalently. The term linker can be applied to a molecule to be reacted with two or more other molecules to covalently connect them, or to the group resulting from such reaction with one or both molecules, as will be clear from context. A "bifunctional crosslinker" connects two molecules or groups. A "multifunctional crosslinker" connects three or more molecules or groups. A linker optionally serves to place the at least two molecules or groups in a preferred configuration and/or localization, for example, so that the two molecules can have preferred interactions, e.g., with two different molecules, or two different locations on a single molecule or molecular complex (for example, two linked biotins can have preferred interactions with two adjacent biotin binding sites on a streptavidin tetramer).

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified. Typical polypeptides comprise ten or more, twenty or more, thirty or more, forty or more, or fifty or more amino acid residues.

A "protein" comprises a single polypeptide comprising fifty or more amino acid residues or two or more associated polypeptides collectively comprising fifty or more amino acid residues. A protein optionally has a defined biological function. A protein containing two or more polypeptide subunits can be homomeric (containing identical subunits) or heteromeric (containing two or more different types of subunits).

A "label" is a moiety that facilitates detection, e.g., of a molecule. A label is optionally optically detectable, electrically detectable, enzymatically detectable, electrochemically detectable, and/or detectable based on its mass. Exemplary optically detectable labels include fluorescent labels (e.g., fluorescent dyes, e.g., cyanine-, fluorescein-, or rhodamine-based dyes), luminescent labels, and colorimetric labels. Many labels are commercially available and can be used in the context of the invention.

A variety of additional terms are defined or otherwise characterized herein.

DETAILED DESCRIPTION

In some aspects, the invention provides sets of compounds in which different compounds can be used to label and identify or localize different nucleic acids, proteins, cells, or other molecules, analytes, or targets of interest. Different compounds contain different detectable labels or groups of labels, and are assembled by covalent attachment of protein cores to which the labels are bound. Assembling the labeling compounds from modular protein cores provides ease of synthesis while still permitting flexible control over the type and number of labels in each different compound. Targets (molecules, cells, etc.) labeled with such compounds are also a feature of the invention, as are methods of making and using the modular labeling compounds, methods of making and using molecules labeled with the compounds, and reaction mixtures and systems including the labeling compounds or labeled compounds. Although the following descriptions are provided in terms of protein cores, it will be appreciated that smaller polypeptides can be employed instead of or in addition to proteins as the cores.

One general class of embodiments provides a composition comprising a first compound comprising one or more proteins and one or more label components bound to the proteins, and a second compound comprising two or more covalently linked proteins and two or more label components bound to the proteins. Each of the label components comprises one or more labels. The different compounds include detectably different groups of one or more labels. In some embodiments, the number of labels in the different compounds is different. In a preferred aspect, the total number of labels in the second compound is greater than that in the first compound. In some embodiments, the labels are all identical. In such embodiments, different compounds produce different detectable signals since each compound carries a different number of copies of the label. For example, different compounds bearing different numbers of copies of a fluorescent label are distinguishable from each other by the differing amplitude of fluorescent signal each compound exhibits.

In some embodiments, the labels within the first compound, within the second compound, and/or between the first and second compounds are different. In such embodiments, the different labels, or different combinations of types and numbers of different labels, produce different signals. For example, the first compound can be labeled with one label and the second compound can be labeled with two or more labels, where each of the two or more labels is distinct due to detected emission at one or more wavelengths that is distinguishable from the emission of the other label(s). In this example, the second compound can be distinguished from the first, e.g., by the ratio of detected emission at two or more wavelengths. As another example, in a compound with two or more labels, a second label can quench the fluorescence of the first label. As yet another example, two labels on a compound can exhibit fluorescence resonance energy transfer (FRET), which is a distance-dependent interaction between the excited states of two dye single moieties. In this case, excitation is transferred from the donor to the acceptor moiety without emission of a photon from the donor. The donor and acceptor moieties must be in close proximity (e.g., within about 100 Å). Suitable donor/acceptor pairs include, e.g., fluorescein/tetramethylrhodamine, LAEDANS/fluorescein, EDANS/dabcyl, fluorescein/QSY7 nonfluorescent acceptor, and many others known to one skilled in the art; see, e.g., Johnson and Spence (Eds.), Molecular Probes Handbook: A Guide to Fluorescent Probes and Labeling Technologies, Eleventh Edition (2010). A compound can also include more than one kind of label, e.g., a fluorescent dye and a mass tag.

For greatest ease in assembly of the compounds, the label components on the first and second compounds are identical. As noted, each label component includes one or more label moieties. For example, each label component can comprise a single, identical label. As another example, each label component can include two or more labels (which can be the same or different). In other embodiments, however, the label components on the first and second compounds are different. For example, one type of label component can be used on the first compound while another type is used on the second compound. In other examples, a mixture of different types of label components is used in the first compound and/or in the second compound.

A compound can include essentially any convenient number of label moieties. In some embodiments, a compound of the invention has 1 to 100, 1 to 50, 1 to 20, or 1 to 10 labels, for example, 1, 2, 3, 4, 5, 6, 7, or 8 labels. The labels can be of the same or different types. Similarly, an individual label component can include essentially any convenient number of label moieties. In some embodiments, a label component has 1 to 100, 1 to 50, 1 to 20, or 1 to 10 labels, for example, 1, 2, 3, 4, 5, 6, 7, or 8 labels, of the same or different types.

A variety of labels are known in the art and can be adapted to the practice of the present invention. In one class of embodiments, the labels are optical labels, e.g., a fluorescent, a luminescent, a fluorogenic, a chemiluminescent, a chromophoric, or a chromogenic label, or another label that becomes detectable upon absorption of excitation radiation from an illumination source. Examples of preferred optically detectable labels include, e.g., organic fluorescent labels, such as cyanine-, fluorescein-, and/or rhodamine-based dyes, inorganic labels such as semiconductor nanocrystals, or quantum dots. A wide variety of such detectable labels are generally commercially available (see, e.g., Molecular Probes Handbook: A Guide to Fluorescent Probes and Labeling Technologies, supra). Such labels may be incorporated onto a given molecule alone or in an interactive combination, e.g., as an energy transfer pair such as a donor/quencher pair or a FRET pair. For example, in certain embodiments, the functional groups comprise FRET pairs as described in U.S. Pat. No. 8,927,212, the disclosure of which is incorporated herein by reference in its entirety for all purposes. Additionally, such labels may comprise organic label materials, e.g., organic fluorophores, or inorganic fluorescent or luminescent compounds, such as semiconductor nanocrystals, i.e., fluorescent quantum dots, or the like. Many suitable fluorescent moieties are known in the art; see, e.g., U.S. Pat. No. 9,062,091 and U.S. patent application publications 2012/0077189, 2012/0058482, 2012/0058469, and 2012/0052506, which are incorporated herein by reference in their entirety for all purposes. For exemplary label components including exemplary fluorescent dye moieties, see, e.g., U.S. Pat. No. 9,062,091 and U.S. patent application publications 2017/0145495, 2017/0145496, and 2017/0145502, previously incorporated by reference in their entirety. In some embodiments, different labels are distinguished from each other by their differing fluorescent emission wavelength maxima. In some embodiments, different labels share a fluorescent emission maximum but are nonetheless distinguishable by the amplitude of emission (e.g., where one label produces a signal with a brightness of 1× while the other label produces a signal with a brightness of 1.5×). Other examples of labels include particles that are optically detectable through their ability to scatter light. Such particles include any of the particle types described elsewhere, herein, and particularly, metal nanoparticles, e.g., gold, silver, platinum, cobalt, or the like, which may be detected based upon a variety of different light scatter detection schemes, e.g., Rayleigh/Mie light scattering, surface enhanced Raman scattering, or the like. Other suitable labels include, but are not limited to, electrically detectable labels, enzymatically detectable labels, electrochemically detectable labels, and labels detectable based upon their mass. Mass labels include, e.g., particles or other large moieties that provide detectable variations in mass of the molecule to which they are attached or vary the molecule's rotational diffusion. Electrochemical labels that detectably alter the charge of the molecule, magnetic labels, such as magnetic particles, or the like can be employed. Other examples of suitable labels include groups that affect the flow of current, i.e., groups that alter (e.g., enhance or reduce) impedance or conductance of the composition. Such labels are useful, e.g., in applications where incorporation is detected by changes in conductance or impedance, e.g., in nanopore-based nucleic acid sequencing applications or nanoFET-based nucleic acid sequencing applications. Examples of conductance impacting functional groups include, e.g., long alkane chains which optionally include solubility enhancing groups, such as amido substitutions; long polyethylene glycol chains; polysaccharides; particles, such as latex, silica, polystyrene, metal, semiconductor, or dendrimeric particles; branched polymers, such as branched alkanes, branched polysaccharides, branched aryl chains; highly charged groups or polymers; oligopeptides; and oligonucleotides. Useful labels may additionally or alternatively include electrochemical groups that may be detected or otherwise exploited for their electrochemical properties, such as their overall electric charge. For example, highly charged groups can be included, like additional phosphate groups, sulfate groups, amino acid groups or chains, e.g., polylysine, polyarginine, etc. Likewise, redox active groups, such as redox active compounds, e.g., heme, or redox active enzymes, can be included. Other label types may include, e.g., magnetic particles that may be sensed through appropriate means, e.g., magneto-tunnel junction sensors, etc.

Attachment of the labels and the label components to the proteins can be by any suitable means. In one class of embodiments, the label components are noncovalently bound to the proteins. For example, the label component can include one member of an affinity binding pair while the protein comprises the other member. A variety of affinity binding pairs are readily applied to the compositions of the invention and include, for example, avidin/biotin pairs (including, e.g., avidin, neutravidin and streptavidin, or associative fragments or subunits thereof) or other biotin-binding protein/biotin pairs, antibody/antigen or epitope pairs, complementary nucleic acid pairs, nucleic acid and nucleic acid binding protein pairs, associative protein or polypeptide pairs, carbohydrate/lectin pairs, GST/glutathione pairs, RNA/aptamer pairs, and the like. Other types of affinity binding pairs are known in the art. Further, methods for the production of members of specific binding pairs are provided in the art, e.g., in U.S. Pat. No. 5,733,743, incorporated herein by reference in its entirety for all purposes. For purposes of the present invention, an affinity binding pair will typically possess a dissociation constant of less than $1\times10^{-3}$M, preferably less than $1\times10^{-4}$M, less than $1\times10^{-5}$M, less than $1\times10^{-6}$M, less than $1\times10^{-7}$M, less than $1\times10^{-8}$M, less than $1\times10^{-9}$M, less than $1\times10^{-10}$M, and in some particularly preferred cases, less than $1\times10^{-15}$M. In most preferred aspects, the dissociation constant of the affinity coupling will be between $1\times10^{-5}$M and $1\times10^{-16}$M, depending upon the application for which the compositions are desired.

In a preferred class of embodiments, the proteins are biotin-binding proteins, e.g., a tetrameric biotin-binding protein or a dimeric biotin-binding protein. A tetrameric biotin-binding protein is optionally tetravalent, having four active biotin binding sites. In other embodiments, a tetrameric biotin-binding protein has three, two, or one active biotin binding site(s) (and one, two, or three inactive sites, respectively). Similarly, a dimeric biotin-binding protein is optionally divalent, having two active biotin binding sites. In other embodiments, a dimeric biotin-binding protein has one active biotin binding site (and one inactive site). Multimeric biotin-binding proteins can be homomeric or heteromeric (e.g., a streptavidin tetramer, or a tetramer comprising three streptavidin subunits and one traptavidin subunit).

Suitable biotin-binding agents are well known in the art and can be used with the methods and compositions provided herein. Streptavidin is a biotin-binding agent that has been cloned and studied extensively. See, for example, Argaraña, et al. (1986) Nucleic Acids Res. 14(4): 1871-1882; Aslan, et al. (2007) Journal of Biotechnology 128: 213-225; Aslan, et al. (2005) J. Proc. Natl. Acad. Sci. USA 102(24):8507-8512; Baugh, et al. (2010) Biochemistry 49:4568-4570; Gitlin, et al. (1988) Biochem. J. 256:279-282; Hendrickson, et al. (1989) Proc. Natl. Acad. Sci. USA 86:2190-2194; Hyster, et al. (2012) Science 338:500-503; Klumb, et al. (1998) Biochemistry 37(21):7657-63; Kurzban, et al. (1991) J. Biol. Chem. 266(22):14470-14477; Matsumoto, et al. (2011) J. Biotechnology 152:37-42; Sano, et al. (1996) Annals of the New York Academy of Sciences 799 (Enzyme Engineering XIII) pp. 383-390; Schmidt, et al. (1994) Journal of Chromatography A 676:337-345; Srisawat, et al. (2001) RNA 7:632-641; Tahiri-Alaoui, et al. (2002) Nucleic Acids Res. 30(10):e45; Voss, et al. (1997) Protein Engineering 10(8):975-982; and Wilbur, et al. (2004) Bioconjugate Chem. 15:1454-1463, all of which are incorporated herein by reference in their entireties for all purposes. Production of heteromeric biotin-binding proteins that include both active and inactive subunits has been described, e.g., in Fairhead et al. (2014) J. Am. Chem. Soc. 136: 12355-12363 and Howarth et al. (2006) Nat Methods 3: 267-273. The dimeric biotin-binding protein rhizavidin has also been described; see, e.g., Helpploainen et al. (2007) Biochem. J. 405: 397-405. Although many of the compositions, methods, examples, and applications described herein comprise the use or inclusion of streptavidin, e.g., for binding to biotinylated label components and/or targets, it will be understood that other biotin-binding agents (e.g., proteins, nucleic acids, or other molecules or molecular complexes) can also be used, e.g., avidin, deglycoslylated avidin (NeutrAvidin), traptavidin, tamavidin, rhizavidin, and variants, mutants, or derivatives thereof. For example, U.S. Pat. No. 7,981,632 describes the "strep-tag" peptide, which binds to a modified version of streptavidin, streptactin. The present invention contemplates using the reagents provided herein in combination with streptactin and/or the strep-tag. For example, streptactin can be substituted for streptavidin in applications where bis-biotin moieties can be bound to streptactin instead of single biotin moieties; alternatively, one or more strep-tag peptides can be linked to a reactant which is subsequently bound to streptactin, or to streptavidin where binding is strong enough. Linking of strep-tags to reactants can be accomplished using conventional molecular biology techniques, cloning, chemical synthesis, and the like. Yet further, peptide and nucleic acid aptamers having an affinity for streptavidin have also been developed and described in the art, e.g., in Tahiri-Alaoui, et al. (2002) Nuc. Ac. Res. 30(10):e45; and Wilson, et al. (2001) Proc. Natl. Acad. Sci. USA 98:3750-3755, both of which are incorporated herein by reference in their entireties for all purposes. Such streptavidin-binding aptamers can be linked to reactants to facilitate binding to streptavidin in a manner similar to the biotin tags described herein. For example, two linked aptamers on a single reactant can operate in a manner similar to a bis-biotin tag and provide a means of linking the reactant to two binding sites on a streptavidin molecule. Similarly, analogs or modified forms of biotin capable of binding streptavidin, avidin, or another biotin-binding agent can be employed, e.g., in a multi- or bis-tag, e.g., a biotin sulfoxide (see, e.g., Garlick and Giese (1990) "Dissociative binding of alpha- and beta-sulphoxides of biotinylamido-ethyl-3-(4-hydroxy-3-[125I]iodophenyl)propionamide to avidin" Biochemical Journal 268(3):611-613), iminobiotin, desthiobiotin (also known as dethiobiotin), oxybiotin, carbobiotin (see, e.g., Wormser et al. (1972) "Synthesis and Growth-Promoting Activity of dl-cis-Hexahydro-4-(4-carboxybutyl)-2-cyclopentimidazolone: Carbobiotin" Journal of Pharmaceutical Sciences 61(7):1168-1170), selenobiotin, carboxybiotin, homobiotin, norbiotin, diaminobiotin, biotin sulfone, epibiotin, 5-hydroxybiotin, 2-thiobiotin, azabiotin, methylated derivatives of biotin (e.g., biotin methyl ester), and/or ketone biotin. For crystal structures of various biotin analogs and modified forms, see, e.g., DeTitta et al. (1980) "Carboxybiotin translocation mechanisms suggested by diffraction studies of biotin and its vitamers" Proc Natl Acad Sci USA. 77(1):333-7 and Stallings and DeTitta (1985) "Crystallographic investigations of biotin and carboxybiotin derivatives" Ann N Y Acad Sci. 447:152-68. As such, recitation of streptavidin and biotin in various embodiments herein is merely exemplary and in no way excludes the use of other biotin- or streptavidin-binding reactants or of other biotin forms or analogs, either instead of or in combination with streptavidin and/or biotin, in the various aspects of the invention described herein, e.g., methods, compositions, and kits. As such, embodiments are contemplated that comprise different combinations of binding partners in the same complex, e.g., a reactant having a single biotin tag and a single streptavidin-binding aptamer, where the reactant binds to a streptavidin tetramer, with the aptamer bound to one binding site in one dimer of the tetramer, and the biotin bound to the other binding site in the same dimer.

In embodiments in which the proteins are biotin-binding proteins, the label component(s) typically comprise a biotin moiety. Optionally, the label component comprises a bis-biotin moiety. For exemplary suitable bis-biotin moieties, see U.S. patent application publication 2017-0184580, herein incorporated by reference in its entirety for all purposes. Typically, the bis-biotin moiety binds to two biotin binding sites on a single biotin-binding protein. In one class of embodiments, the proteins are tetravalent biotin-binding proteins, and each label component comprises a bis-biotin moiety bound to two biotin binding sites on one of the tetravalent biotin-binding proteins. In other embodiments, one or more label components are bound to the biotin-binding proteins via a bis-biotin moiety while one or more other label components are bound via a biotin moiety. In other embodiments, each label component comprises a single biotin moiety.

In another class of embodiments, the label components are covalently bound to the proteins. Optionally, the label component includes a linker that connects the label(s) and the protein. Covalent linkage of moieties to proteins is well known in the art. The reactive groups on various amino acids can be used to provide specific sites of attachment, for a label component or another moiety of interest (e.g., another protein, a nucleotide component, a molecule of interest, or the like). Reactive groups for the attachment of moieties to the protein include amine groups on lysine or arginine, the thiol group on cysteine, the acid group on aspartic acid or glutamic acid, and the hydroxyl group on serine or threonine. In some cases, an available protein will have appropriate residues for connection of the moieties. In other cases, the appropriate residues can be engineered into the protein. Using genetic engineering to produce a desired protein having various amino acids removed or added is a common and well understood practice.

The different reactivity of different groups on the protein can be used to direct specific moieties to different attachment points on the protein. For example, a nucleotide moiety can be connected to a specific cysteine at one desired attachment point, and a fluorescent moiety can be attached to a lysine at a second attachment point. In some cases, the same type of residue will have different reactivity due to where it resides on the protein, allowing selective attachment. For example, a protein may have three lysine moieties where each has a different reactivity. Attachment can be carried out such that only the most reactive lysine is modified, or alternatively, attachment can be carried out by protecting the two most reactive lysines, then reacting the moiety of interest with the third, least reactive lysine.

There are many types of chemical reactions that can be used to react with specific amino acid residues on proteins. For example, coupling through the cysteine thiol can be accomplished using a reaction with maleimide. Cysteine groups can also be coupled with allylic halides, phenylmethyl halides, alkyl halides, or alpha-halo carbonyl groups.

Amine groups can be coupled to activated carboxylates or activated sulfonic acids. Amine or carboxylate functionality on the protein can be used to produce amide linkages. Linkages containing nitrogen double bonds such as oxime or hydrazones can be used. Highly selective linkages can be formed using cycloaddition chemistry such as the Huisgen 1,3-dipolar azide-alkyne cycloaddition. See, e.g., Kalia and Raines (2010) "Advances in Bioconjugation" Curr Org Chem. 14(2): 138-147, Besanceney-Webler et al. (2011) "Increasing the Efficacy of Bioorthogonal Click Reactions for Bioconjugation" Angew. Chem. Int. Ed. 50:8051-8056, and DiMarco et al. (2010) International Journal of Nanomedicine 5:37-49.

The moieties can be attached to the protein through unnatural amino acids that are introduced into the protein, allowing for specific attachment chemistry. See, for example, the work of Peter Schultz, e.g., Noren et al. (1989) "A general method for site-specific incorporation of unnatural amino acids into proteins" Science 244:182-188 and Ellman et al. (1991) "Biosynthetic method for introducing unnatural amino acids site-specifically into proteins" Methods in Enzymology 202: 301-336.

Many other methods of chemically modifying proteins are known in the art. See e.g. "Chemical modification of proteins at cysteine: opportunities in chemistry and biology" Chalker J M, Bernardes G J, Lin Y A, Davis B G, Chem Asian J. 2009 May 4; 4(5):630-40, "Chemoselective ligation and modification strategies for peptides and proteins" Hackenberger C P, Schwarzer D. Angew Chem Int Ed Engl. 2008; 47(52):10030-74, "Chemoselective modification of proteins: hitting the target", Carrico I S, Chem Soc Rev. 2008 July; 37(7):1423-31, "Modification of tryptophan and tryptophan residues in proteins by reactive nitrogen species", Yamakura F, Ikeda K, Nitric Oxide. 2006 March; 14(2):152-61, Chemical modification of proteins, Came A F, Methods Mol Biol. 1994; 32:311-20, Selective chemical modification of proteins, Shaw E, Physiol Rev. 1970 April; 50(2):244-96, and "Chemical reagents for protein modification" By Roger L. Lundblad, CRC Press, 2004.

Reactive functional groups can be used to attach proteins to proteins, moieties to proteins, moieties to linkers, and/or linkers to proteins. Reactions for this purpose and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and derivatives thereof including, but not limited to activated esters, e.g., N-hydroxysuccinimide esters, N-hydroxyphthalimide, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;
(b) hydroxyl groups, which can be converted to esters, sulfonates, phosphoramidates, ethers, aldehydes, etc.
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, allowing derivatization via formation of carbonyl derivatives, e g, imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds; and (k) phosphoramidites and other standard functional groups useful in nucleic acid synthesis. A combination of covalent and noncovalent linkages for different label components can also be employed.

The number of labels can be selected and readily tested for performance. In general, having more than one label can be used to obtain higher signal, e.g., more than one dye can be used to obtain higher brightness, but as is known in the art, the addition of one more dye does not always increase the brightness commensurate with the number of dyes. Those of skill in the art will understand how to attach the dyes or other labels and choose the number of dyes or other labels with the best performance for a given system. The type of linkers used to attach the labels, including the length of the linker and its chemical functionality, can also be used to engineer the appropriate label performance. See, e.g., U.S. Pat. No. 9,062,091 and U.S. patent application publications 2017/0145495, 2017/0145496, and 2017/0145502, hereby incorporated by reference in their entirety.

As noted above, the two or more proteins in the second compound are covalently linked. The first compound can also include two or more proteins, which are optionally covalently linked. The proteins in the various compounds are generally covalently joined by a linkage other than a standard peptide bond.

In some embodiments, the proteins are covalently linked by at least one isopeptide bond. For example, one protein can include a SpyTag while a second protein is fused with a SpyCatcher domain; contacting the two proteins under appropriate conditions results in formation of an isopeptide bond between the SpyTag and SpyCatcher. For a discussion of the SpyTag/SpyCatcher system, see, e.g., Zakeri et al. (2012) "Peptide tag forming a rapid covalent bond to a protein, through engineering a bacterial adhesin" Proc Natl Acad Sci USA 109(12):E690-7; see also U.S. Pat. No. 9,547,003. Fusion proteins including a SnoopTag or Snoop-Catcher or other similar system can be similarly employed; see Veggiani et al. (2016) "Programmable polyproteams built using twin peptide superglues" Proc Natl Acad Sci USA 113(5):1202-7 and Brune et al. (2017) "Dual Plug-and-Display Synthetic Assembly Using Orthogonal Reactive Proteins for Twin Antigen Immunization" Bioconjugate Chem. 28:1544-1551. In embodiments in which tetrameric biotin-binding proteins are employed, mixed tetramers in which at least one subunit includes a tag or catcher domain can be employed. Similarly, in embodiments in which dimeric biotin-binding proteins are employed, mixed dimers in which at least one subunit includes a tag or catcher domain can be employed.

In some embodiments, the proteins are covalently linked through at least one bifunctional or multifunctional cross-linker. Exemplary reactive groups on proteins that can be employed for attachment of the crosslinker have been detailed above. Compatible reactive groups can be included on the crosslinker, separated by nonreactive spacing groups (e.g., polyethylene glycol (PEG), peptides, carbohydrate polymers, or alkyl chains). Suitable reactive groups on the protein and crosslinker include, e.g., thiol/maleimide, thiol/iodoacetamide, thiol/iodoacetate, amine/NHS, and click chemistry groups, as well as those listed hereinabove. Exemplary suitable multifunctional crosslinkers include, but are not limited to, tris-(2-maleimidoethyl)amine, tetrakis-(3-maleimidopropyl)pentaerythritol, tris-succinimidyl aminotriacetate, tris-succinimidyl (6-aminocaproyl)aminotriacetate, and tetrakis-(N-succinimidylcarboxypropyl) pentaerythritol. As another example, the protein can include a SpyTag while the crosslinker includes two or more Spy-Catchers, or the protein can include a SpyCatcher while the crosslinker includes SpyTags. SnoopTag and SnoopCatcher, or other similar systems, can also be employed.

In some embodiments, the proteins are covalently joined without a linker, e.g., through a disulfide bond, through a bond formed by a pair of the reactive functional groups detailed above, or the like. As noted, the proteins are generally covalently joined by a linkage other than a standard peptide bond. In some embodiments, however, the proteins are joined by a standard peptide bond, e.g., produced by enzymatic ligation, enzymatic coupling, or the like, after the two proteins have been separately produced and optionally modified and/or bound to one or more components. Suitable systems for coupling proteins through a post-translational peptide bond include sortases, inteins (particularly split inteins), and similar transpeptidase activities. For description of sortase systems, see, e.g., Matsumoto et al. (2011) "Site-specific tetrameric streptavidin-protein conjugation using sortase A" Journal of Biotechnology 152:37-42, Williamson et al. (2012) "Efficient N-terminal labeling of proteins by use of sortase" Angew Chem Int Ed Engl. 51(37):9377-80, and Guimaraes et al. (2013) "Site-specific C-terminal and internal loop labeling of proteins using sortase-mediated reactions" Nat Protoc. 8(9):1787-99, each of which is hereby incorporated by reference in its entirety. For description of intein systems, see, e.g., Iwai et al. (2006) "Highly efficient protein trans-splicing by a naturally split DnaE intein from *Nostoc punctiforme*" FEBS Lett. 580(7):1853-8, Zettler et al. (2009) "The naturally split Npu DnaE intein exhibits an extraordinarily high rate in the protein trans-splicing reaction" FEBS Lett. 583(5):909-14, and Demonte et al. (2015) "Postsynthetic Domain Assembly with NpuDnaE and SspDnaB Split Inteins" Appl Biochem Biotechnol. 177(5):1137-51, each of which is hereby incorporated by reference in its entirety. It will be evident that such covalently linked proteins are not equivalent to a fusion protein (a single polypeptide chain produced by transcription and translation from a recombinant gene including coding sequences for both proteins). Joining the two (or more) proteins after their production can facilitate production of compounds that cannot readily be produced from a fusion protein. For example, two biotin-binding proteins can be bound to different ligands (e.g., nucleotide and/or label components) and then covalently linked to each other to produce a defined compound, whereas mixing a fusion protein containing the two biotin-binding proteins with the ligands would result in a mixture of the desired product and undesired products since the biotin binding sites are identical.

Combinations of techniques for joining proteins can also be employed. As just one example, a first and a second protein can be joined by a bifunctional linker while the second protein is joined to a third protein through an isopeptide bond.

As described above, in preferred embodiments, the proteins are biotin-binding proteins. In other embodiments, essentially any suitable protein known in the art can be employed. For example, the protein can comprise the protein ubiquitin. Ubiquitin is a small regulatory protein that has been found in almost all tissues of eukaryotic organisms. A variety of different modifications can occur. The ubiquitin protein has about 76 amino acids and has a molecular mass of about 8.5 kDa. It is highly conserved among eukaryotic species: Human and yeast ubiquitin share 96% sequence identity. Any suitable ubiquitin protein can be used as the protein or as part of the protein. For example, the human ubiquitin 1UBQ can be used by coupling label component(s) or other moieties to reactive groups on the protein as described herein. For example, mutation of the native lysines to arginines results in a unique reactive amine at the N-terminus, and addition of a cysteine residue near the C-terminus provides a unique reactive thiol. See, e.g. Vijay-Kumar et al. (1987) J. Mol. Biol. 194: 531-544, incorporated herein by reference in its entirety for all purposes. In some cases, the ubiquitin will have a his tag such as a hexa-his tag at its N- or C-terminus. A sequence for ubiquitin is provided, e.g., in U.S. Pat. No. 9,062,091, as are a variety of useful mutant forms of ubiquitin.

The protein TOP7 can also be employed. Top7 is an artificial 93-residue protein that was designed to have a unique fold not found in nature. See Kuhlman et al. (2003) "Design of a novel globular protein fold with atomic-level accuracy" Science 302 (5649):1364-1368, U.S. patent application Ser. No. 12/429,930, and U.S. Pat. No. 7,574,306, each incorporated herein by reference in their entirety for all purposes. As described above, the various residues can be mutated to allow for specific attachment of one or more crosslinkers, label components (e.g., dye components), or molecules of interest (e.g., nucleotides) to the protein. A sequence for TOP7 is provided, e.g., in U.S. Pat. No. 9,062,091, as are a variety of useful mutant forms of TOP7.

Coiled-coils of alpha helices, or single, stable alpha helices, provide particularly efficient means by which to generate two widely separated points of attachment in a protein scaffold. An example of a coiled-coil is provided by thermostable seryl tRNA synthetase from *Pyrococcus horikoshii* (PKSERRS) as shown in its crystal structures (for example, Protein Data Bank database ID 2ZR2). The coiled-coil domain of seryl tRNA synthetases can be transplanted into different protein scaffolds, as shown by the crystal structure of dynein-seryl tRNA synthetase (Protein Data Bank ID 3ERR). The coiled-coil domain of a serine tRNA synthetase can be used as or in the protein component of a compound of the invention. This domain has a rigid structure that can provide separation between various moieties, e.g., dye and nucleotide components. The coil structure can be fused to the terminus of a single domain protein. A mutation such as a cysteine can be incorporated into the tip of the coiled coil domain, to which can be attached one or more moieties (e.g., crosslinkers, label components, or molecules of interest). One or more other moieties can be attached to a more distant portion of the coil coiled domain or to the protein to which the domain is fused. Other suitable proteins include proteins engineered to include Leucine Rich Repeats such as Ankyrin repeats, Cyanoverin, and Protein G. As another example, a stable helix in solution can be generated by using a repeat of the sequence EAAAR (Huyghes-Despointes, et al. 1993).

As noted, particularly useful proteins for the invention include biotin-binding proteins including, e.g., avidin, streptavidin, tamavidin, traptavidin, xenavidin, neutravidin, bradavidin, AVR2, AVR4, and homologs thereof. In some cases, the monomeric, dimeric, or tetrameric forms can be used. In particular, the tetrameric form in combination with bis-biotin linked label (e.g., dye) components and/or molecules of interest (e.g., nucleotide components) are useful. In some cases, glycosylation variants of the proteins are used. The protein can be based on or include the protein tamavidin and its homologs. Tamavidin is a fungal avidin-like protein that binds biotin with high affinity. See e.g. RCSB Protein Data Bank protein code 2ZSC and Takakura, et al., Journal: (2009) 276: 1383-1397, incorporated herein by reference in its entirety. Tamavidin may be mutated; for example, C135 can be mutated in case the cysteine would have some unwanted reactivity. In some cases, tamavidin will be constructed to have a his tag at its N or C terminus. Tamavidin can be advantageous in that it can be more stable than streptavidin and can be more soluble in *E. coli* expression. One particularly useful protein is streptavidin, and in particular in the tetrameric form. Sequences of the monomeric polypeptides that make up the tetrameric tamavidin and streptavidin proteins are provided, e.g., in U.S. Pat. No. 9,062,091.

Papain can also be employed as the protein or part of the protein in compounds of the invention. Papain, also known as *papaya* proteinase I, is a cysteine protease enzyme present in *papaya*. Proteins in the papain family, which are present in many species, can also be employed. Papain includes lysines and a reactive cysteine in the active site. As described above, amino acid sites can be mutated to provide the appropriate sites for attachment of desired components.

Another suitable protein for use is maltose binding protein. Maltose binding protein is a part of the maltose/maltodextrin system of *Escherichia coli*, which is responsible for the uptake and efficient catabolism of maltodextrins. Maltose binding protein has an approximate molecular mass of 42.5 kilodaltons. Wild type maltose binding protein includes lysines but has no cysteines; however, residues have been mutated in the literature to generate cysteines (e.g., S337C, N100C, and/or S233C).

The SNAP-tag protein can also be employed as the protein or part of the protein in compounds of the invention. SNAP-tag is a 20 kDa mutant of the DNA repair protein O6-alkylguanine-DNA alkyltransferase that reacts specifically and rapidly with benzylguanine (BG) derivatives, leading to irreversible labeling of the SNAP-tag with a synthetic probe. SNAP-tag protein has about 184 residues. See, for example, RCSB Protein Data Bank code 3KZZ. In some cases, one or more moieties (e.g., crosslinkers, labels, or molecules of interest) are attached to a benzylguanine derivate, then reacted with the SNAP-tag protein. Additional moieties can be attached to the SNAP tag protein, e.g., by reaction with side chains as detailed above.

Another type of protein that can be a protein or component thereof in the compounds is a beta lactamase. Beta lactamases are enzymes produced by some bacteria that confer resistance to beta-lactam antibiotics. The beta lactamases react by opening up the beta lactam ring in the antibiotic. In some embodiments, a beta lactamase suicide inhibitor is used to connect one or more moieties (e.g., crosslinkers, labels, or molecules of interest) to the beta lactamase. Additional moieties can be attached to the beta lactamase, e.g., by reaction with side chains as detailed above. For example, the beta lactamase inhibitor clavulanic acid attached to one or more dyes can be reacted with a beta lactamase attached to one or more nucleotides to produce a labelled nucleotide analog. The attachments to the protein are preferably arranged in order to prevent contact between the dyes and a polymerase enzyme associated with one of the nucleotide substituents. Suitable beta lactamases include cephalosporinases, penicillinases, carbenicillinases, and carbapenamases.

The protein can be modified, for example, at the C-terminal and/or N-terminal region of the protein. For example, the one or more modifications can be a polyhistidine tag, a HIS-10 tag, a HIS-6 tag, a polyglutamate tag, a Glu10 tag, an alanine tag, an Ala10 tag, an Ala 16 tag, a biotin tag, a GST tag, a biotin ligase recognition sequence or other biotin attachment site (e.g., a BiTag or a Btag or variant thereof, e.g., BtagV1-11; see, e.g., US patent application publication 2012-0034602), an S Tag, a SNAP-tag, an HA tag, a DSB (Sso7D) tag, a lysine tag, a NanoTag, a Cmyc tag, a tag or linker comprising the amino acids glycine and serine, a tag or linker comprising the amino acids glycine, serine, alanine and histidine, a tag or linker comprising the amino acids glycine, arginine, lysine, glutamine and proline, a sortase recognition peptide (e.g., LPXTG or LPXTA), a split intein N- or C-terminal sequence (e.g., from *Nostoc punctiforme* DnaE), a plurality of polyhistidine tags, a plurality of HIS-10 tags, a plurality of HIS-6 tags, a plurality of alanine tags, a plurality of Ala10 tags, a plurality of Ala16 tags, a plurality of biotin tags, a plurality of GST tags, a plurality of biotin tags, a plurality of S Tags, a plurality of SNAP-tags, a plurality of HA tags, a plurality of DSB (Sso7D) tags, a plurality of lysine tags, a plurality of NanoTags, a plurality of Cmyc tags, a plurality of tags or linkers comprising the amino acids glycine and serine, a plurality of tags or linkers comprising the amino acids glycine, serine, alanine and histidine, a plurality of tags or linkers comprising the amino acids glycine, arginine, lysine, glutamine and proline, biotin, avidin, one or more Factor Xa sites, one or more enterokinase sites, thrombin sites, antibodies or antibody domains, antibody fragments, antigens, receptors, receptor domains, receptor fragments, ligands, or combinations thereof. The protein can include one or more modifications at both the C-terminal and N-terminal regions of the polymerase, where such features at the C-terminal and N-terminal regions are optionally the same, e.g., a polyhistidine tag (e.g., a His10 tag) at both the C-terminal and N-terminal regions. Proteins that include exogenous or heterologous features at both the C-terminal and N-terminal regions optionally include a B-Tag and a polyhistidine tag (e.g., a B-Tag at the N-terminal region and a polyhistidine tag (e.g., a His-10 tag) at the C-terminal region). Any of these modifications can be used as sites for attachment of one or more moieties. Various suitable attachment chemistries have been noted above and/or are well known in the art. As one example, a protein bearing a sortase tag can be coupled to a moiety (e.g., a nucleotide component or label component) that bears a glycine with a free amino group, by a suitable sortase.

The composition optionally includes additional compounds. As for the first and second compounds, any additional compounds can be distinguished from other compounds in the set by the type and/or number of labels therein. In one exemplary class of embodiments, the composition comprises a third compound comprising two or more covalently linked proteins and three or more label components bound to the proteins, each label component comprising one or more labels. Optionally, the total number of labels in the third compound is greater than that in the second compound (which is optionally greater than that in the first compound). The composition optionally also includes a fourth compound comprising three or more covalently linked proteins and four or more label components bound to the proteins, each label component comprising one or more labels. Optionally, the total number of labels in the fourth compound is greater than that in the third compound. Optionally, the first compound comprises one label component, the second compound comprises two label components, the third compound comprises three label components, and the fourth compound comprises four label components. A single type of label component or different types of label components can be employed, and each label component can include a single, identical label, two or more identical labels, or different labels, as detailed above. Optionally, a single type of label is employed, the second compound includes twice as many label moieties as the first compound, the third compound includes three times as many label moieties as the first compound, and the fourth compound includes four times as many label moieties as the first compound (e.g., one, two, three, and four labels, or two, four, six, and eight label moieties, for the first, second, third, and fourth compounds, respectively).

In one exemplary class of embodiments, the first compound comprises one protein and one label component, the second compound comprises two covalently linked proteins and two label components, the third compound comprises two covalently linked proteins and three label components, and the fourth compound comprises three covalently linked proteins and four label components. Optionally, the label components on the first, second, third, and fourth compounds are identical. In a preferred class of embodiments, the proteins are tetravalent biotin-binding proteins and the label components are bound to the proteins via bis-biotin moieties. In other embodiments, the proteins are divalent biotin-binding proteins and the label components are bound via biotin moieties.

Targets (e.g., cells, complexes, analytes, molecules, or locations) of interest labeled with the compounds of the invention are also features of the invention. Accordingly, in one class of embodiments, the first compound is bound to at least one first molecule of interest, and the second compound is bound to at least one second molecule of interest. Essentially any desired molecules can be labeled using the compounds of the invention. For example, the first molecule of interest can be a first antibody specific for a first epitope, and the second molecule of interest can be second antibody specific for a second epitope. Typically, the first and second epitopes are different. As another example, the first molecule of interest can be a first nucleotide while the second molecule of interest is a second nucleotide, typically different from the first. A molecule of interest is optionally (but not necessarily) part of a complex, e.g., a protein-protein complex, protein-nucleic acid complex, enzyme-substrate complex, or the like.

Compounds can be covalently bound to the molecules or other targets of interest, for example, through reactive functional groups or crosslinkers as detailed above. In other embodiments, the compounds are noncovalently bound to the molecules of interest or other targets, for example, through affinity binding pairs as detailed above. As one specific example, the proteins can be tetravalent biotin-binding proteins, and each molecule of interest can comprise a bis-biotin moiety bound to two biotin binding sites on one of the tetravalent biotin-binding proteins. In other examples, the molecules of interest are bound via biotin moieties.

Where a compound includes two or more proteins, the label components and molecules of interest can be attached to the proteins in essentially any convenient arrangement. For example, where a compound comprises two proteins, two molecules of interest, and two label components, the two molecules of interest can be bound to one of the proteins and the two label components to the other protein, or one of the molecules of interest and one of the label components can be bound to one of the proteins while the other molecule of interest and the other label component are bound to the other protein. Many other arrangements will be immediately evident to one of skill, depending on the number of proteins, label components, and molecules of interest and the number of species bound to each protein. In some cases, maintaining separation between various components attached to the protein(s) can be advantageous. For example, as described in U.S. Pat. No. 9,062,091, for nucleotide analogs including a nucleotide and a fluorescent dye, separating the dye component from the nucleotide component can prevent or reduce photodamage to a polymerase enzyme incorporating the nucleotide into a growing nucleic acid strand. Separation can be achieved, for example, by attaching one component at the N-terminus of a protein and the other component at the C-terminus of the protein, attaching the two components to different covalently linked proteins, or otherwise ensuring that the two attachment points are spaced apart by a suitable distance (e.g., for a nucleotide analog, by a distance such that when a nucleoside phosphate attached to the protein is in the active site of the polymerase enzyme, a fluorescent dye moiety attached to the protein is shielded by the protein from coming into contact with the polymerase enzyme).

Molecules labeled with labeling compounds of the invention find use in a variety of applications. For example, the labeling compounds are particularly useful for single molecule detection, e.g., of proteins or other analytes as described in US patent application publication 2014/0342468 or of target molecules in zero mode waveguides (ZMWs) or other optical confinements. For a discussion of ZMWs, see, e.g., U.S. Pat. Nos. 6,917,726, 7,056,676, 7,056,661, 7,052,847, and 7,033,764, US patent application publication 2003/0044781, Levene et al. (2003) "Zero-mode waveguides for single-molecule analysis at high concentrations" Science 299:682-686, and Eid et al. (2009) "Real-time DNA sequencing from single polymerase molecules" Science 323:133-138, each of which is incorporated herein by reference in its entirety for all purposes. Such single molecule detection can be applied, for example, in single molecule sequencing as described in greater detail hereinbelow.

In one aspect, the invention provides labeled nucleotide analogs, e.g., dye-labeled nucleotide analogs. Sets of labeled nucleotide analogs (e.g., one, two, three, or four analogs, e.g., having one analog corresponding to each base A, C, T, and G or A, C, U, and G and distinguishable by fluorescent emission wavelength(s) and/or amplitude(s)) find use in applications such as single molecule sequencing, e.g., by monitoring incorporation of labeled nucleotide analogs in real time as described in greater detail hereinbelow.

Accordingly, one general class of embodiments provides a set of dye-labeled nucleotide analogs that includes a first labeled nucleotide analog comprising one or more proteins, one or more first nucleotide components bound to the proteins, and one or more dye components bound to the proteins. The set typically also includes a second labeled nucleotide analog comprising two or more covalently linked proteins, one or more second nucleotide components bound to the proteins, and two or more dye components bound to the proteins. Each dye component comprises one or more dye moieties. The different analogs preferably include detectably different groups of one or more dye labels. In some embodiments, the number of dye moieties in the different analogs is different. In a preferred aspect, the total number of dye moieties in the second analog is greater than that in the first analog. In some embodiments, the dye moieties are all identical. In such embodiments, different analogs produce different detectable signals since each analog carries a different number of copies of the dye. For example, different analogs bearing different numbers of copies of a fluorescent dye moiety are distinguishable from each other by the differing amplitude of fluorescent signal each analog exhibits.

In some embodiments, the dye moieties within the first analog, within the second analog, and/or between the first and second analogs are different. In such embodiments, the different dye moieties, or different combinations of types and numbers of different dye moieties, produce different signals. For example, the first analog can be labeled with one dye and the second analog can be labeled with two or more dyes, where each of the two or more dyes is distinct due to detected emission at one or more wavelengths that is distinguishable from the emission of the other dye(s). In this example, the second analog can be distinguished from the first, e.g., by the ratio of detected emission at two or more wavelengths. As another example, in an analog with two or more dye labels, a second label can quench the fluorescence of the first dye. As yet another example, two dye moieties on an analog can exhibit FRET, as noted above.

For greatest ease in assembly of the analogs, the dye components on the first and second analogs are identical. As noted, each dye component includes one or more dye moieties. For example, each dye component can comprise a single, identical dye moiety. As another example, each dye component can include two or more dye moieties (which can be the same or different). In other embodiments, however, the dye components on the first and second analogs are different. For example, one type of dye component can be used on the first analog while another type is used on the second analog. In other examples, a mixture of different types of dye components is used in the first analog and/or in the second analog.

A nucleotide analog can include essentially any convenient number of dye moieties. In some embodiments, an analog of the invention has 1 to 100, 1 to 50, 1 to 20, or 1 to 10 dye moieties, for example, 1, 2, 3, 4, 5, 6, 7, or 8 dye moieties. The dye moieties can be of the same or different types. Similarly, an individual dye component can include essentially any convenient number of dye moieties. In some embodiments, a dye component has 1 to 100, 1 to 50, 1 to 20, or 1 to 10 dye moieties, for example, 1, 2, 3, 4, 5, 6, 7, or 8 dye moieties, of the same or different types. The number of dye moieties can be selected and readily tested for performance. In general, having more than one dye moiety can be used to obtain higher signal, e.g., more than one dye can be used to obtain higher brightness, but as is known in the art, the addition of one more dye does not always increase the brightness commensurate with the number of dyes. Those of skill in the art will understand how to attach the dyes and choose the number of dyes with the best performance for a given system. The type of linkers used to attach the dyes, including the length of the linker and its chemical functionality, can also be used to engineer the appropriate label performance.

As described above, a variety of suitable dye moieties are known in the art and can be adapted the practice of the present invention. In one class of embodiments, the dye moieties are fluorescent dye moieties. Examples of fluorescent dyes are well known in the art, including but not limited to cyanine-, fluorescein-, and/or rhodamine-based dyes. A wide variety of such dyes are generally commercially available. See, e.g., Molecular Probes Handbook: A Guide to Fluorescent Probes and Labeling Technologies, supra. Such labels may be incorporated onto a given molecule alone or in an interactive combination, e.g., as an energy transfer pair such as a donor/quencher pair or a FRET pair, e.g., as described in U.S. Pat. No. 8,927,212. Many suitable fluorescent dye moieties are known in the art; see, e.g., U.S. Pat. No. 9,062,091 and U.S. patent application publications 2012/0077189, 2012/0058482, 2012/0058469, and 2012/0052506, previously incorporated by reference. For exemplary dye components including fluorescent dye moieties, see, e.g., U.S. Pat. No. 9,062,091 and U.S. patent application publications 2017/0145495, 2017/0145496, and 2017/0145502, previously incorporated by reference in their entirety.

Attachment of the dye components and nucleotide components to the proteins can be by any suitable means, as detailed above. In one class of embodiments, the dye and/or nucleotide components are noncovalently bound to the proteins. For example, the dye and/or nucleotide component can include one member of an affinity binding pair while the protein comprises the other member. A variety of affinity binding pairs are readily applied to the compositions of the invention and include, for example, avidin/biotin pairs (including, e.g., avidin, neutravidin and streptavidin, or associative fragments or subunits thereof) or other biotin-binding protein/biotin pairs, antibody/antigen or epitope pairs, complementary nucleic acid pairs, nucleic acid and nucleic acid binding protein pairs, associative protein or polypeptide pairs, carbohydrate/lectin pairs, GST/glutathione pairs, RNA/aptamer pairs, and the like, as described above.

In a preferred class of embodiments, the proteins are biotin-binding proteins, e.g., a tetrameric biotin-binding protein or a dimeric biotin-binding protein. A tetrameric biotin-binding protein is optionally tetravalent, having four active biotin binding sites. In other embodiments, a tetrameric biotin-binding protein has three, two, or one active biotin binding site(s). Similarly, a dimeric biotin-binding protein is optionally divalent, having two active biotin binding sites. In other embodiments, a dimeric biotin-binding protein has one active biotin binding site. Multimeric biotin-binding proteins can be homomeric or heteromeric (e.g., a streptavidin tetramer, or a tetramer comprising three streptavidin subunits and one traptavidin subunit).

Suitable biotin-binding agents are well known in the art; see, e.g., the references hereinabove. Suitable biotin-binding proteins include, but are not limited to, streptavidin, avidin, deglycoslylated avidin (NeutrAvidin), traptavidin, tamavidin, rhizavidin, and variants, mutants, or derivatives thereof.

In embodiments in which the proteins are biotin-binding proteins, the dye and/or nucleotide component(s) typically comprise a biotin moiety. Optionally, the dye and/or nucleotide component comprises a bis-biotin moiety. For exemplary suitable bis-biotin moieties, see U.S. patent application publication 2017-0184580, previously incorporated by reference in its entirety. Typically, the bis-biotin moiety binds to two biotin binding sites on a single biotin-binding protein. In one class of embodiments, the proteins are tetravalent biotin-binding proteins, and each component comprises a bis-biotin moiety bound to two biotin binding sites on one of the tetravalent biotin-binding proteins. In other embodiments, one or more components are bound to the biotin-binding proteins via a bis-biotin moiety while one or more other dye and/or nucleotide components are bound via a biotin moiety.

In one class of embodiments, the dye and/or nucleotide components are covalently bound to the proteins. Covalent linkage of moieties to proteins is well known in the art. As detailed above, reactive groups on various amino acids can be used to provide specific sites of attachment, for a dye component, nucleotide component, or the like. A combination of covalent and noncovalent linkages for different components can also be employed.

Optionally, the dye component includes a linker that connects the dye(s) and the protein. Similarly, the nucleotide component optionally includes a linker that connects the nucleotide(s) and the protein. The linker for the dye component or nucleotide component can have any suitable molecular structure. It can include, for example, alkanes, hydroxyls, phosphates, peptides, glycols, or saccharide linkages. It is generally preferred that a polar or hydrophilic linker be used in order to enhance water solubility. The length of the linker can be selected in order to allow the moiety freedom to move with respect to the protein to which it is covalently or noncovalently connected, but to prevent contact of a fluorescent moiety with a polymerase when the nucleotide moiety is associated with the polymerase.

Polar and ionic groups are also often added to portions of the nucleotide analog in order to improve water solubility, as most sequencing reactions are carried out in aqueous environments. For example, carboxylic acid groups, sulfate groups, sulfonate groups, phosphate groups and/or amine groups can be added to the dye moieties, bis-biotin moieties, phospholinked nucleotide moieties, or other portions of the nucleotide analog to ensure adequate aqueous solubility. In some embodiments, one or more sulfonate ($—SO_3^-$) groups are attached to the linkers, in particular the linkers connecting phospholinked nucleotide moieties to the protein. One particularly useful way to introduce sulfonate groups into the nucleotide analog is to include one or more six membered aromatic rings each having multiple sulfonate groups attached to it, for example, a six membered aromatic ring having 2, 3, 4, or 5 sulfonate groups attached.

In some cases, the rigidity of the linker is controlled in order to hold the relevant component in the appropriate position. For example, rigid components such as connected aromatic rings can be used in order to control the rigidity of the linker. Another way to control the rigidity of the linker and the position of a dye or nucleotide is to use a nucleic acid linker such as DNA or a derivative thereof such as PNA. For example, it is known that stretches of double stranded DNA can be relatively rigid, allowing for controlling the position of the component attached thereto. In some embodiments, the linkers comprise double-stranded nucleic acid portions such as double-stranded DNA portions.

Exemplary linkers are described, e.g., in U.S. Pat. No. 9,062,091 and U.S. patent application publications 2017/0145495, 2017/0145496, and 2017/0145502, previously incorporated by reference.

Each nucleotide component comprises at least one nucleotide moiety. The nucleotide moiety can be attached to the protein through essentially any convenient position of the nucleotide moiety, e.g., on the base, sugar, or phosphate portion. In one particularly useful class of embodiments, the nucleotide moiety is attached to the protein through the polyphosphate portion of the nucleotide (i.e., is "phospholinked"). With this type of attachment, when the nucleotide monophosphate portion of the nucleotide analog is incorporated into a growing nucleic acid strand, the portion of the nucleotide analog having the protein and the fluorescent dye is cleaved from the portion of the nucleotide that gets incorporated, and diffuses away to allow for incorporation of the next nucleotide into the chain without interference with these moieties.

A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, e.g., other than A, G, C, T, or U, though upon incorporation into an oligonucleotide, the resulting residue in the oligonucleotide can be the same as (or different from) an A, G, C, T, or U residue. Modifications to the analogs can include extending the phosphate chains, e.g., to include a tetra-, penta-, hexa-, or heptaphosphate group. An analog can include substitution of one or more non-bridging oxygen in the polyphosphate, for example with S or $BH_3$, and/or substitution of a bridging oxygen in the polyphosphate, for example with a methylene or substituted methylene. Analogs optionally comprise one or more substituent on a phosphate, sugar, or base moiety of the nucleoside or nucleotide relative to a naturally occurring nucleoside or nucleotide. In some embodiments, the nucleotide analog includes three phosphate containing groups; for example, the analog can be a labeled nucleoside triphosphate analog and/or an α-thiophosphate nucleotide analog having three phosphate groups. In some embodiments, a nucleotide analog includes one or more extra phosphate containing groups, relative to a nucleoside triphosphate. For example, the analog can include four, five, six, or seven phosphate groups, as noted above.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytosine, uracil, and in some cases, inosine. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the base group neither a purine nor a pyrimidine.

In the analogs, the sugar typically provides a suitable backbone for a synthesizing nucleic acid strand. For example, the sugar moiety is optionally selected from a D-ribosyl, 2' or 3' D-deoxyribosyl, 2', 3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional nucleoside triphosphates, is preferably coupled to the 5' hydroxyl group, as in natural nucleoside triphosphates. However, in some cases, the phosphorus containing chain is linked to the sugar group by the 3' hydroxyl group.

It is important for many real-time single molecule systems that the nucleotide moiety be phospholinked. In this way, the cleavage of the alpha-beta phosphodiester bond in the nucleotide analog releases the labeled component. Thus, as noted above, the nucleotide moiety is optionally attached to the protein (and, e.g., to any linker included in the nucleotide component and linking the nucleotide to the protein) through its polyphosphate portion.

A nucleotide analog can include essentially any convenient number of nucleotide moieties, e.g., phospholinked nucleotide moieties. For example, the nucleotide analog can have from about 1 to about 100 nucleotide moieties, about 1 to 50 nucleotide moieties, about 1 to about 18 nucleotide moieties, or 1, 2, 3, 4, 5, 6, 7, 8, 9, 10, 11, 12, 13, 14, 15, 16, 17, or 18 nucleotide moieties. In some cases, the nucleotide analog has at least about 1 to about 18 phospholinked nucleotide moieties, or at least about 1, 2, 3, 4, 5, 6, 7, 8, 9, 10, 11, 12, 13, 14, 15, 16, 17, or 18 phospholinked nucleotide moieties. Raising the number of nucleotide moieties tends to raise the effective concentration of the nucleotide at the enzyme. As is well known in the art, the concentration of nucleotide can be varied in order to control the polymerase kinetics, and that depending on the system and the desired performance, the concentration of the nucleotide can be varied both by controlling the amount of nucleotide analog per volume and by controlling the number of nucleotides per nucleotide analog. For example, where a larger analog (e.g., an analog comprising a greater number of proteins) exhibits slower kinetics than smaller analogs employed therewith, one or more additional nucleotide moieties can be added to the larger analog to compensate for this effect (e.g., by incorporating one or more nucleotide components having multiple nucleotide moieties connected to a multifunctional linker into the analog, as described herein). Those of skill in the art will understand how to use the compounds of the invention to optimize system performance. The lists of potential choices described herein for the numbers and types of moieties can be combined with any of the described numbers and types of dye moieties described. Similarly, an individual nucleotide component can include essentially any convenient number of nucleotide moieties, e.g., phospholinked nucleotide moieties. In some embodiments, a nucleotide component has 1 to 100, 1 to 50, 1 to 20, or 1 to 10 nucleotide moieties, for example, 1, 2, 3, 4, 5, 6, 7, or 8 nucleotide moieties, typically (but not necessarily) of the same type (e.g., corresponding to A, C, G, or T).

Typically, different nucleotide analogs include different nucleotide moieties that comprise different nucleobases. For example, a set of four analogs can be provided, where one analog corresponds to A, one to T, one to G, and one to C. Different analogs are typically detectably distinguishable through different dyes, different numbers of dye moieties, and/or different combinations of dye moieties, as detailed above.

For exemplary nucleotide components, including nucleotide components having multiple nucleotide moieties connected to a multifunctional linker, see, e.g., U.S. Pat. No. 9,062,091 and U.S. patent application publications 2017/0145495, 2017/0145496, and 2017/0145502.

As noted above, the two or more proteins in the second analog are covalently linked. The first analog can also include two or more proteins, which are optionally covalently linked. The proteins in the various analogs are generally covalently joined by a linkage other than a standard peptide bond. In one class of embodiments, the proteins are covalently linked by at least one isopeptide bond. For example, one protein can include a SpyTag while a second protein is fused with a SpyCatcher domain; contacting the two proteins under appropriate conditions results in formation of an isopeptide bond between the SpyTag and SpyCatcher, as described above. SnoopTag and SnoopCatcher, or other similar systems, can also be employed. In embodiments in which tetrameric biotin-binding proteins are employed, mixed tetramers in which at least one subunit includes a tag or catcher domain can be employed. Similarly, in embodiments in which dimeric biotin-binding proteins are employed, mixed dimers in which at least one subunit includes a tag or catcher domain can be employed. In another class of embodiments, the proteins are covalently linked through at least one bifunctional or multifunctional crosslinker. Exemplary reactive groups on proteins that can be employed for attachment of the crosslinker and exemplary crosslinkers have been detailed above. In other embodiments, the proteins are covalently joined without a linker, e.g., through a disulfide bond, through a bond formed by a pair of the reactive functional groups detailed above, or the like.

As described above, in preferred embodiments, the proteins are biotin-binding proteins, for example, avidin, streptavidin, tamavidin, traptavidin, xenavidin, neutravidin, bradavidin, AVR2, AVR4, and homologs thereof. In other embodiments, essentially any suitable protein known in the art can be employed. Examples include, but are not limited to, ubiquitin, TOP7, coiled-coils of alpha helices, single alpha helices, papain, maltose binding protein, SNAP-tag protein, beta lactamase, and the like, as detailed hereinabove. Also as noted above, the protein can be modified, for example, at its C-terminal and/or N-terminal region.

The set optionally includes additional analogs. As for the first and second analogs, any additional analogs can be distinguished from other analogs in the set by the type and/or number of labels therein. In one exemplary class of embodiments, the set comprises a third analog comprising two or more covalently linked proteins and three or more dye components bound to the proteins, each dye component comprising one or more dye moieties. Optionally, the total number of dye moieties in the third analog is greater than that in the second analog (which is optionally greater than that in the first analog). The set optionally also includes a fourth analog comprising three or more covalently linked proteins and four or more dye components bound to the proteins, each dye component comprising one or more dye moieties. Optionally, the total number of dye moieties in the fourth analog is greater than that in the third analog. Optionally, the first analog comprises one dye component, the second analog comprises two dye components, the third analog comprises three dye components, and the fourth analog comprises four dye components. A single type of dye component or different types of dye components can be employed, and each dye component can include a single, identical dye moiety, two or more identical dye moieties, or different dye moieties, as detailed above. Optionally, a single type of dye moiety is employed, the second analog includes twice as many dye moieties as the first analog, the third analog includes three times as many dye moieties as the first analog, and the fourth analog includes four times as many dye moieties as the first analog (e.g., one, two, three, and four dye moieties, or two, four, six, and eight dye moieties, for the first, second, third, and fourth analogs, respectively).

In one exemplary class of embodiments, the first analog comprises one protein and one dye component, the second analog comprises two covalently linked proteins and two dye components, the third analog comprises two covalently linked proteins and three dye components, and the fourth analog comprises three covalently linked proteins and four dye components. Optionally, the dye components on the first, second, third, and fourth analogs are identical. Optionally, the first analog comprises one first nucleotide component, the second analog comprises two second nucleotide components, the third analog comprises one third nucleotide component, and the fourth analog comprises two fourth nucleotide components. In a preferred class of embodiments, the proteins are tetravalent biotin-binding proteins and the dye and nucleotide components are bound to the proteins via bis-biotin moieties. In other embodiments, the proteins are divalent biotin-binding proteins and the dye and nucleotide components are bound via biotin moieties.

The dye components and nucleotide components can be attached to the proteins in essentially any convenient arrangement, e.g., where an analog includes two or more proteins. For example, where an analog comprises two proteins, two nucleotide components, and two dye components, the two nucleotide components can be bound to one of the proteins and the two dye components to the other protein, or one of the nucleotide components and one of the dye components can be bound to one of the proteins while the other nucleotide component and the other dye component are bound to the other protein. Many other arrangements will be immediately evident to one of skill, depending on the number of proteins, dye components, and nucleotide components and the number of species bound to each protein. Arrangements can be selected, for example, to facilitate synthesis or assembly of the analogs and/or as desirable for performance of the analogs (e.g., kinetic behavior or other performance in a sequencing reaction). For example, as noted above and as described in U.S. Pat. No. 9,062,091, separating the dye component from the nucleotide component can prevent or reduce photodamage to a polymerase enzyme incorporating the nucleotide into a growing nucleic acid strand. Separation can be achieved, for example, by attaching one component at the N-terminus of a protein and the other component at the C-terminus of the protein, attaching the two components to different covalently linked proteins, or otherwise ensuring that the two attachment points are spaced apart by a suitable distance (e.g., for a nucleotide analog, by a distance such that when a nucleoside phosphate attached to the protein is in the active site of the polymerase enzyme, a fluorescent dye moiety attached to the protein is shielded by the protein from coming into contact with the polymerase enzyme). In one example, a dye component is bound to a tetravalent biotin-binding protein through a bis-biotin moiety bound to two biotin binding sites and a nucleotide component is bound to the tetravalent biotin-binding protein through a bis-biotin moiety bound to the other two biotin binding sites, resulting in separation of the components by the protein.

It will be evident that, where biotin-binding proteins are employed, all available biotin binding sites can but need not be occupied. Biotin binding site(s) not required for attachment of a dye component or nucleotide component can remain unoccupied, or an unneeded site can be blocked by binding of a biotin moiety that is not associated with a dye component or nucleotide component. Biotin-binding proteins that are heteromers of subunits with active biotin binding sites and subunits lacking active binding sites can also be employed.

An exemplary set of dye-labeled nucleotide analogs based on tetrameric biotin-binding protein cores is illustrated in FIGS. 1A-1B. The components employed to assemble the analogs are shown in FIG. 1A: a streptavidin tetramer (SA), a tetramer including three streptavidin subunits and one subunit that has a SpyTag fused to streptavidin (SA-1Tag), a tetramer including three streptavidin subunits and one subunit that has a SpyCatcher fused to streptavidin (SA-1Catcher), a tetramer including two streptavidin subunits and two subunits that have a SpyCatcher fused to streptavidin (SA-2Catcher), a nucleotide component comprising a phospholinked nucleotide and a bis-biotin moiety, and a dye component that comprises a fluorescent dye moiety and a bis-biotin moiety. Although one nucleotide component is illustrated for clarity, four different nucleotide components are employed, one corresponding to each base A, C, G, and T. FIG. 1B illustrates four exemplary analogs formed from these components. One analog includes a streptavidin tetramer, an A nucleotide component bound to the streptavidin through its bis-biotin moiety, and a dye component bound to the streptavidin through its bis-biotin moiety. A second analog includes two protein cores, SA-1Tag and SA-1Catcher, that are covalently linked by an isopeptide bond formed by the SpyTag and SpyCatcher. This analog also includes two T nucleotide components and two dye components, each bound through a bis-biotin moiety. A third analog includes two protein cores, SA-1Tag and SA-1Catcher, covalently linked by an isopeptide bond, one C nucleotide component, and three dye components. Each of the nucleotide and dye components is bound through a bis-biotin moiety. A fourth analog includes three protein cores, two SA-1Tag tetramers and one SA-2Catcher tetramer. Each of the tagged tetramers is covalently linked to the catcher tetramer through an isopeptide bond. This analog also includes two G nucleotide components and four dye components, each bound through a bis-biotin moiety. The four analogs can be distinguished and identified by the different amplitude of fluorescent signal produced by the one, two, three, or four copies of the dye on the respective analogs. It will be evident that similar analogs can be produced by reversing the placement of the SpyTag and SpyCatcher on streptavidins, resulting in SA-1Catcher, SA-1Tag, and SA-2Tag as the protein cores.

Figure 2B:
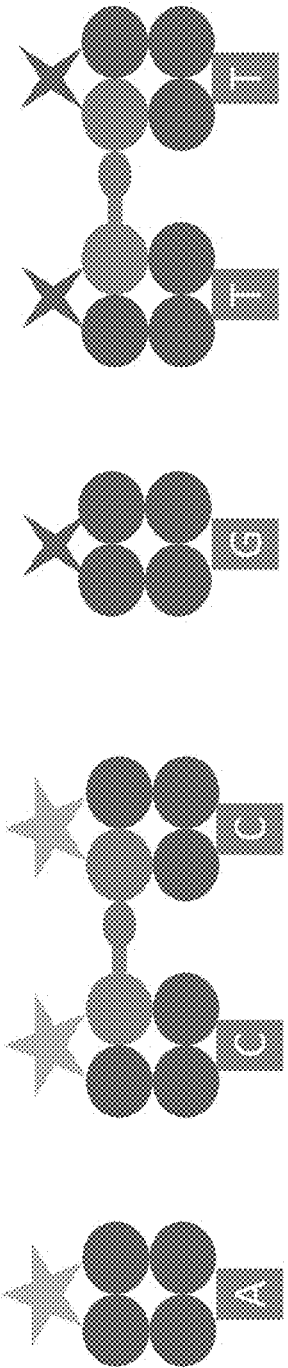
FIG. 2B illustrates an exemplary set of modular nucleotide analogs distinguishable by a combination of the wavelength and amplitude of signal from two fluorescent dyes.

Another exemplary set of dye-labeled nucleotide analogs is illustrated in FIGS. 2A-2B. The components employed to assemble the analogs are shown in FIG. 2A: a streptavidin tetramer (SA), a tetramer including three streptavidin subunits and one subunit that has a SpyTag fused to streptavidin (SA-1Tag), a tetramer including three streptavidin subunits and one subunit that has a SpyCatcher fused to streptavidin (SA-1Catcher), and a nucleotide component comprising a phospholinked nucleotide and a bis-biotin moiety. Although one nucleotide component is illustrated for clarity, four different nucleotide components are employed, one corresponding to each base A, C, G, and T. Two dye components are also employed. Each dye component includes one of two different fluorescent dye moieties and a bis-biotin moiety. The two dyes have different emission wavelength profiles. FIG. 2B illustrates four exemplary analogs formed from these components. One analog includes a streptavidin tetramer, an A nucleotide component bound to the streptavidin through its bis-biotin moiety, and a first dye component bound to the streptavidin through its bis-biotin moiety. A second analog includes two protein cores, SA-1Tag and SA-1Catcher, that are covalently linked by an isopeptide bond formed by the SpyTag and SpyCatcher. This analog also includes two C nucleotide components and two first dye components, each bound through a bis-biotin moiety. A third analog includes a streptavidin tetramer, a G nucleotide component bound to the streptavidin through its bis-biotin moiety, and a second dye component bound to the streptavidin through its bis-biotin moiety. A fourth analog includes two protein cores, SA-1Tag and SA-1Catcher, covalently linked by an isopeptide bond, two T nucleotide components, and two second dye components. Each of the nucleotide and dye components is bound through a bis-biotin moiety. The four analogs can be distinguished and identified by the different amplitude and characteristic wavelength of the fluorescent signal produced by the dyes on the analogs.

Figure 3:
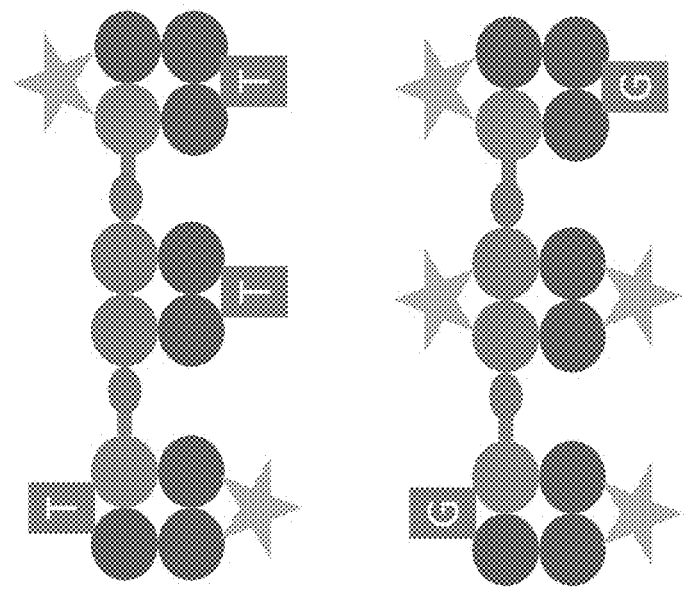
FIG. 3 illustrates an exemplary set of modular, multi-amplitude nucleotide analogs distinguishable by the amplitude of signal from a single type of fluorescent dye.
Figure 3:
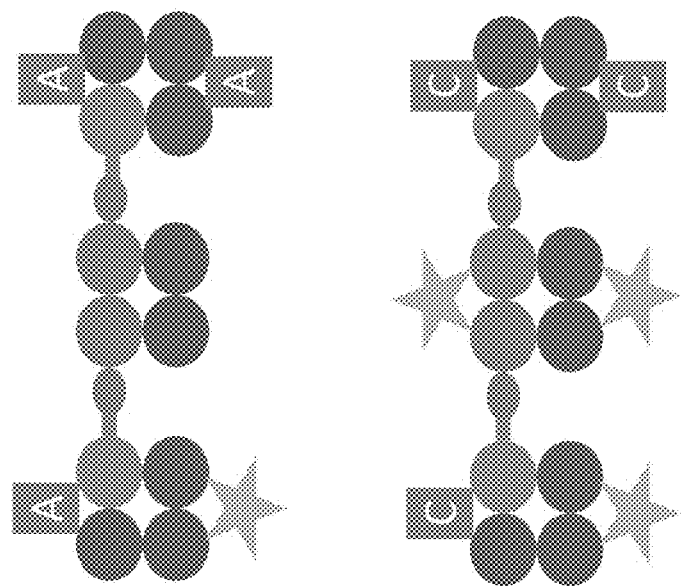

An exemplary set of analogs using identical protein cores is illustrated in FIG. 3. The components employed to assemble the analogs include a tetramer including three streptavidin subunits and one subunit that has a SpyTag fused to streptavidin (SA-1Tag), a tetramer including two streptavidin subunits and two subunits that have a SpyCatcher fused to streptavidin (SA-2Catcher), nucleotide components each comprising a phospholinked nucleotide and a bis-biotin moiety, and a dye component that comprises a fluorescent dye moiety and a bis-biotin moiety. All four analogs have a core that includes two SA-1Tag tetramers and one SA-2Catcher tetramer. Each of the tagged tetramers is covalently linked to the catcher tetramer through an isopeptide bond. One analog includes three A nucleotide components and one dye component. A second analog includes three T nucleotide components and two dye components. A third analog includes three C nucleotide components and three dye components. A fourth analog includes two G nucleotide components and four dye components. Each of the dye and nucleotide components is bound through a bis-biotin moiety. Biotin binding sites not required for attachment of a dye component or nucleotide component can remain unoccupied, be blocked by binding of a biotin moiety that is not associated with a dye component or nucleotide component, or be inactive, as noted above. The four analogs can be distinguished and identified by the different amplitude of fluorescent signal produced by the one, two, three, or four copies of the dye on the respective analogs.

Another exemplary set of dye-labeled nucleotide analogs based on tetrameric biotin-binding protein cores where the proteins are covalently linked through a bifunctional or multifunctional crosslinker is illustrated in FIGS. 4A-4B. The components employed to assemble the analogs are shown in FIG. 4A: a streptavidin tetramer (SA), a tetramer including three streptavidin subunits and one subunit that has a reactive group (SA-1 xm), a nucleotide component comprising a phospholinked nucleotide and a bis-biotin moiety, a dye component that comprises a fluorescent dye moiety and a bis-biotin moiety, and a set of crosslinkers. Although one nucleotide component is illustrated for clarity, four different nucleotide components are employed, one corresponding to each base A, C, G, and T. Three crosslinkers are provided, one bifunctional, one trifunctional, and one quadrifunctional, including two, three, or four copies (respectively) of a reactive group compatible with that on the protein (e.g., a thiol group on the protein and maleimide on the crosslinkers, a SpyCatcher on the protein and a SpyTag on the crosslinkers, etc.). FIG. 4B illustrates four exemplary analogs formed from these components. One analog includes a streptavidin tetramer, an A nucleotide component bound to the streptavidin through its bis-biotin moiety, and a dye component bound to the streptavidin through its bis-biotin moiety. A second analog includes two SA-1xm protein cores that are covalently linked through a bifunctional crosslinker. This analog also includes two T nucleotide components and two dye components, each bound through a bis-biotin moiety. A third analog includes three SA-1xm protein cores covalently linked through a trifunctional crosslinker, three C nucleotide components, and three dye components. Each of the nucleotide and dye components is bound through a bis-biotin moiety. A fourth analog includes four SA-1xm protein cores covalently linked through a quadrifunctional crosslinker. This analog also includes four G nucleotide components and four dye components, each bound through a bis-biotin moiety. The four analogs can be distinguished and identified by the different amplitude of fluorescent signal produced by the one, two, three, or four copies of the dye on the respective analogs.

It will be evident that various crosslinkers and reactive proteins can be employed to produce similar analogs. For example, an analog could instead include two SA-1xm protein cores each covalently linked to a central SA-2xm protein core through a bifunctional crosslinker, or it could include two SA-1xm protein cores and two SA-2xm protein cores joined through a total of three bifunctional crosslinkers.

Systems (e.g., sequencing systems), kits, and reaction mixtures including the compositions of the invention are also features of the invention, as are methods employing the compositions (e.g., methods of sequencing nucleic acids, detecting target analytes, and the like) and methods of making the compositions.

In one aspect, the invention provides a reaction mixture for sequencing a nucleic acid template. The mixture comprises a polymerase enzyme complex comprising a polymerase enzyme, a template nucleic acid, and optionally a primer hybridized to the template nucleic acid. The polymerase enzyme complex is typically immobilized on a surface. The mixture also includes sequencing reagents in contact with the surface, i.e., reagents for carrying out nucleic acid synthesis including a set of labeled nucleotide analogs (e.g., dye-labeled nucleotide analogs) as described herein.

Essentially all of the features noted above apply to these embodiments as well, as relevant, e.g., with respect to number of different analogs included, configuration of the nucleotide analogs (e.g., number, identity, and arrangement of protein cores, label components, labels, nucleotide components, nucleotide moieties, etc.), and the like.

In one aspect, the invention provides a method for sequencing a nucleic acid template. The method includes providing a polymerase enzyme complex comprising a polymerase enzyme, a template nucleic acid, and optionally a primer hybridized to the template nucleic acid, wherein the polymerase enzyme complex is immobilized on a surface; adding sequencing reagents in contact with the surface comprising reagents for carrying out nucleic acid synthesis including a set of labeled nucleotide analogs (e.g., dye-labeled nucleotide analogs) as described herein; and determining the sequential addition of nucleotides to a nucleic acid strand complementary to a strand of the template nucleic acid by observing the interaction of the labeled nucleotide analogs with the polymerase enzyme complex.

Essentially all of the features noted above apply to these embodiments as well, as relevant, e.g., with respect to number of different analogs employed, configuration of the nucleotide analogs (e.g., number, identity, and arrangement of protein cores, label components, labels, nucleotide components, nucleotide moieties, etc.), and the like.

In one aspect, the invention provides a system for sequencing nucleic acids. The system comprises a chip comprising a plurality of polymerase enzyme complexes bound thereto. Each polymerase enzyme complex is individually optically resolvable, and each polymerase enzyme complex comprises a polymerase enzyme, a template nucleic acid, and optionally a primer hybridized to the template nucleic acid. The chip includes sequencing reagents in contact with its surface, comprising reagents for carrying out nucleic acid synthesis including a set of labeled nucleotide analogs (e.g., dye-labeled nucleotide analogs) as described herein. The system also includes an illumination system for illuminating the polymerase enzyme complexes, an optical detection system for detecting fluorescence from the labeled nucleotide analogs while they are interacting with the polymerase enzyme complexes, and a computer for analyzing the signals detected by the detection system to determine the sequential addition of nucleotides to a nucleic acid strand complementary to a strand of the template nucleic acid.

Essentially all of the features noted above apply to these embodiments as well, as relevant, e.g., with respect to number of different analogs included, configuration of the nucleotide analogs (e.g., number, identity, and arrangement of protein cores, label components, labels, nucleotide components, nucleotide moieties, etc.), and the like.

The methods, systems, reaction mixtures, and compositions of the invention are particularly useful for single molecule sequencing, and specifically single molecule sequencing by incorporation in real time. For sequencing processes that rely upon monitoring of the incorporation of nucleotides into growing nascent strands being synthesized by the complex, the progress of the reaction through these steps is of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

Figure 5A:
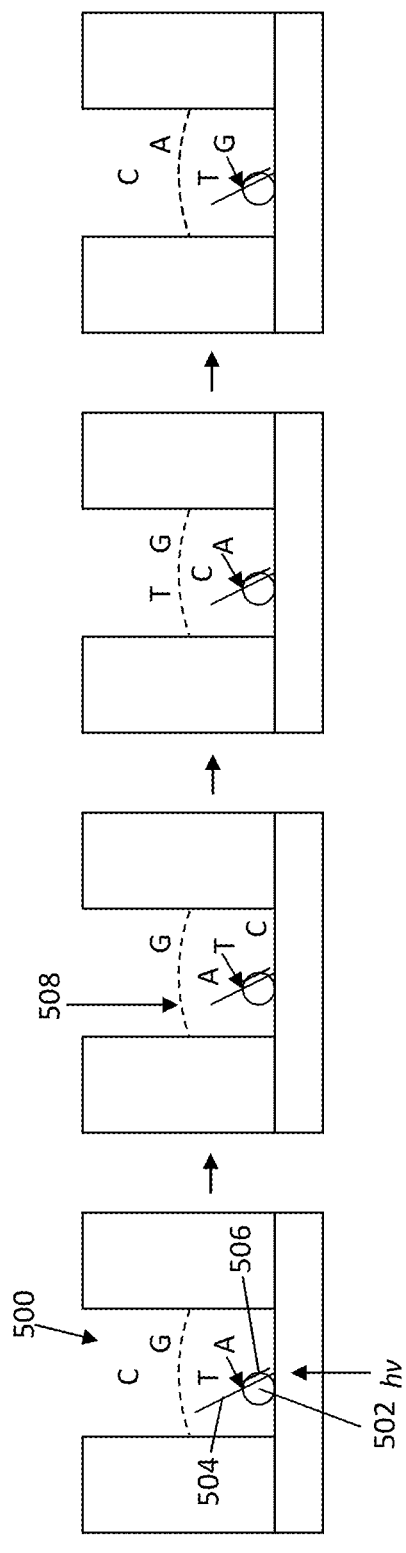
FIGS. 5A-5B schematically illustrate an exemplary single molecule sequencing by incorporation process in which the compositions of the invention provide particular advantages.

In a first exemplary technique, as schematically illustrated in FIG. 5A, a nucleic acid synthesis complex, including a polymerase enzyme 502, a template sequence 504 and a complementary primer sequence 506, is provided immobilized within an observation region 500, that permits illumination (as shown by hv) and observation of a small volume that includes the complex without excessive illumination of the surrounding volume (as illustrated by dashed line 508). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

Figure 5B:
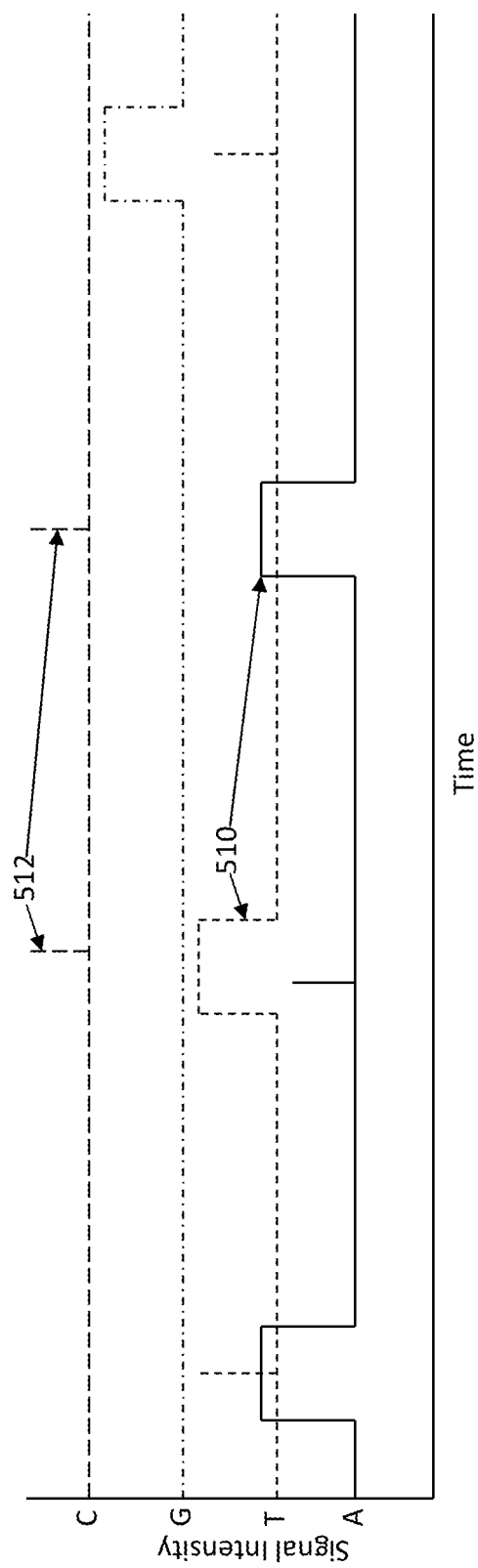

In particular, as shown in FIG. 5B, when a nucleotide, e.g., A, is incorporated into by the polymerase, it is retained within the observation volume for a prolonged period of time, and upon continued illumination yields a prolonged fluorescent signal (shown by peak 510). By comparison, randomly diffusing and not incorporated nucleotides remain within the observation volume for much shorter periods of time, and thus produce only transient signals (such as peak 512), many of which go undetected, due to their extremely short duration.

In particularly preferred exemplary systems, the confined illumination volume is provided through the use of arrays of optically confined apertures termed zero-mode waveguides (ZMWs), e.g., as shown by confined reaction region 500. See, e.g., U.S. Pat. No. 6,917,726, which is incorporated herein by reference in its entirety for all purposes. For sequencing applications, the DNA polymerase is typically provided immobilized upon the bottom of the ZMW. See, e.g., Korlach et al., PNAS U.S.A. 105(4): 1176-1181. (2008), which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuses away from the complex following incorporation of the associated nucleotide, nor do such labels interfere with the incorporation event. See, e.g., Korlach et al., Nucleosides, Nucleotides and Nucleic Acids, 27:1072:1083, 2008.

In another exemplary technique, the nucleotides to be incorporated are each provided with interactive labeling components that are interactive with other labeling components provided coupled to, or sufficiently near the polymerase (which labels are interchangeably referred to herein as "complex borne"). Upon incorporation, the nucleotide borne labeling component is brought into sufficient proximity to the complex-borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair or FRET pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal, e.g., quenched or otherwise indicative of energy transfer. Upon incorporation and cleavage of the terminal phosphate groups, e.g., bearing a donor fluorophore, the quenching or other energy transfer is removed and the resulting characteristic fluorescent signal of the donor is observable.

In preferred aspects, the synthesis complexes in such reaction mixtures are arrayed so as to permit observation of the individual complexes that are being so modulated. In arraying individual complexes to be individually optically resolvable, the systems of the invention will position the complexes on solid supports such that there is sufficient distance between adjacent individual complexes as to allow optical signals from such adjacent complexes to be optically distinguishable from each other.

Typically, such complexes will be provided with at least 50 nm and more preferably at least 100 nm of distance between adjacent complexes, in order to permit optical signals, and particularly fluorescent signals, to be individually resolvable. Examples of arrays of individually resolvable molecules are described in, e.g., U.S. Pat. No. 6,787,308.

In some cases, individual complexes may be provided within separate discrete regions of a support, for example on a chip. For example, in some cases, individual complexes may be provided within individual optical confinement structures, such as zero-mode waveguide cores. Examples of such waveguides and processes for immobilizing individual complexes therein are described in, e.g., international patent application publication number WO 2007/123763, the full disclosure of which is incorporated herein by reference in its entirety for all purposes.

The synthesis complexes are typically provided immobilized upon solid supports, and preferably, upon supporting substrates. The complexes may be coupled to the solid supports through one or more of the different groups that make up the complex. For example, in the case of nucleic acid polymerization complexes, attachment to the solid support may be through an attachment with one or more of the polymerase enzyme, the primer sequence and/or the template sequence in the complex. Further, the attachment may comprise a covalent attachment to the solid support or it may comprise a non-covalent association. For example, in particularly preferred aspects, affinity based associations between the support and the complex are envisioned. Such affinity associations include, for example, avidin/streptavidin/neutravidin associations with biotin or biotinylated groups, antibody/antigen associations, GST/glutathione interactions, nucleic acid hybridization interactions, and the like. In some aspects, the complex is attached to the solid support through the provision of an avidin group, e.g., streptavidin, on the support, which specifically interacts with a biotin group that is coupled to the polymerase enzyme. In some aspects, the surface of the support is biotinylated, and an avidin group (e.g., streptavidin) is bound to the support and to a biotin-coupled polymerase enzyme.

The sequencing processes, e.g., using the substrates described above and the compositions or reaction mixtures of the invention, are generally exploited in the context of a fluorescence microscope system that is capable of illuminating the various complexes on the substrate, and obtaining detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate.

Figure 6:
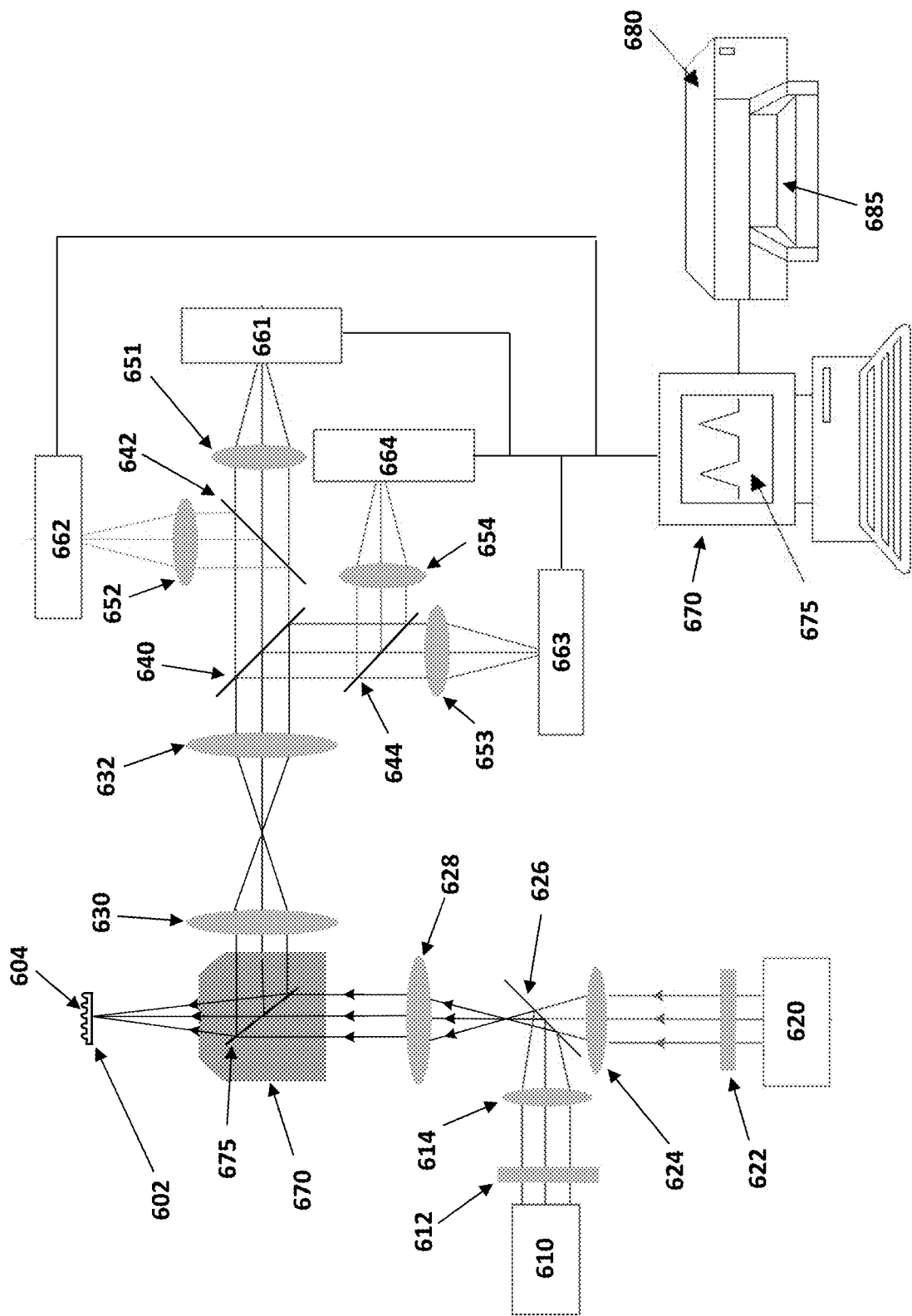
FIG. 6 shows a system for carrying out real-time single molecule sequencing.

One such exemplary system is shown in FIG. 6. An exemplary system is also described in U.S. patent application publication no. 2007-0036511 (see also, e.g., Lundquist et al. (2008) Optics Letters 33:1026-1028), the full disclosure of each of which is incorporated herein by reference in its entirety for all purposes.

Fluorescence reflective optical trains can be used in the applications of the systems of the invention. For a discussion on the advantages of such systems, see, e.g., U.S. Pat. Nos. 7,995,202, 7,692,783, and 7,715,001, the full disclosures of which are incorporated herein by reference in their entirety for all purpose.

For purposes of the present invention, the processes and systems will be described with reference to detection of incorporation events in a real time, sequence by incorporation process, e.g., as described in U.S. Pat. Nos. 7,056,661, 7,052,847, 7,033,764 and 7,056,676 (the full disclosures of which are incorporated herein by reference in their entirety for all purposes), when carried out in arrays of discrete reaction regions or locations. An exemplary sequencing system for use in conjunction with the invention is shown in FIG. 6. As shown, the system includes a substrate 602 that includes a plurality of discrete sources of optical signals, e.g., reaction wells, apertures, or optical confinements or reaction locations 604. In typical systems, reaction locations 604 are regularly spaced and thus substrate 602 can also be understood as an array 602 of reaction locations 604. The array 602 can comprise a transparent substrate having cladding layer on its top surface with an array of nanoscale apertures extending through the cladding to the transparent substrate. This configuration allows for one or more samples to be added to the top surface of the array, and for the array to be observed through the transparent substrate from below, such that only the light from the apertures is observed. The array can be illuminated from below as shown in FIG. 6, and in some embodiments, the array can also be illuminated from above (not shown in FIG. 6).

For illumination from below, one or more excitation light sources, e.g., lasers 610 and 620, are provided in the system and positioned to direct excitation radiation at the various signal sources. Here, two lasers are used in order to provide different excitation wavelengths, for example with one laser 610 providing illumination in the red, and laser 620 providing illumination in the green. The use of multiple laser excitation sources allows for the optimal excitation of multiple labels in a sample in contact with the array. The excitation illumination can be a flood illumination, or can be directed to discrete regions on the array, for example, by breaking the excitation beam into an array of beamlets, each beamlet directed to a feature on the array. In order to break the excitation beams into an array of beamlets, a diffractive optical element (DOE) can be employed. In the system of FIG. 6, the light from excitation sources 610 and 620 is sent through DOE components 612 and 622 respectively. The use of a DOE for providing an array of beamlets is provided, e.g. in U.S. Pat. No. 7,714,303, which is incorporated by reference herein in its entirety. Excitation light is then passed through illumination relay lenses 614 and 624 to interact with dichroic 626. In the system of FIG. 6, the red light from laser 610 is reflected off of dichroic 626, and the green light from laser 620 is directed through the dichroic 626. The excitation light is then passed through illumination tube lens 628 into objective lens 670 and onto the array 602.

Emitted signals from sources 604 are then collected by the optical components, e.g., objective 670, comprising dichroic element 675 which allows the illumination light to pass through and reflects the emitted light. The emitted light passes through collection tube lens 630 and collection relay lens 632. The emitted light is then separated into different spectral channels, and each spectral channel is directed to a different detector. In the system of FIG. 6, the light is separated into four different channels, each channel corresponding predominantly to one of four labels having different wavelength emission maxima to be detected in the sample. Thus, the system allows the user to obtain four two dimensional images, each image corresponding to one of the four labels. In order to separate the light into the four spectral channels, dichroics 640, 642, and 644 are used. Dichroic 640 allows the light for channels 1 and 2 to pass while reflecting the light for channels 3 and 4. Dichroic 642 allows the light for channel 1 to pass, through collection imaging lens 651 to detector 661, and reflects the light for channel 2 through collection imaging lens 652 to detector 662. Dichroic 644 allows the light for channel 3 to pass, through collection imaging lens 653 onto detector 663, and reflects the light for channel 4 through collection illumination lens 654 onto detector 664. Each of the detectors 661-664 comprise arrays of pixels. (It will be evident that where fewer than four wavelengths are to be detected, e.g., where labels are distinguishable by amplitude instead of or in addition to emission wavelength, that fewer dichroics, lenses, and detectors can be employed.) The detectors can be, for example, CMOS, EMCCD, or CCD arrays. Each of the detectors obtains 2-dimensional images of the channel that is directed to that detector. The data from those signals is transmitted to an appropriate data processing unit, e.g., computer 670, where the data is subjected to processing, interpretation, and analysis. The data processing unit is configured to process the data both pixel by pixel and pixel region by pixel region, where each pixel region corresponds to a feature on the substrate. The data processing unit can receive data from calibration runs in order to define software mask pixel weighting, spectral weighting, and noise parameters. These parameters and weightings can be applied to signals that are measured on the detectors during an analytical reaction such as during sequencing. In some embodiments, the data processing unit is configured to define and apply software mask pixel weighting, spectral weighting, and noise parameters that are determined and then applied during an analytical reaction such as during sequencing.

Analyzed and processed signal data obtained from the analytical reactions can ultimately be presented in a user ready format, e.g., on display 675, printout 685 from printer 680, or the like, or may be stored in an appropriate database, transmitted to another computer system, or recorded onto tangible media for further analysis and/or later review. Connection of the detector to the computer may take on a variety of different forms. For example, in preferred aspects, the detector is coupled to an appropriate analog to digital (A/D) converter that is then coupled to an appropriate connector in the computer. Such connections may be standard USB connections, Firewire® connections, Ethernet connections or other high speed data connections. In other cases, the detector or camera may be formatted to provide output in a digital format and be readily connected to the computer without any intermediate components.

This system, and other hardware descriptions herein, are provided solely as a specific example of sample handling and image capture hardware to provide a better understanding of the invention. It should be understood, however, that the present invention includes data analysis and interpretation of a wide variety of real-time florescent detecting systems, including systems that use substantially different illumination optics, systems that include different detector elements (e.g., EB-CMOS detectors, CCD's, etc.), and/or systems that localize a template sequence other than using the zero mode waveguides described herein.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse that carries a distinguishable spectral profile or color.

The present invention can include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

While described in terms of a particular sequencing by incorporation process or system, it will be appreciated that certain aspects of the processes of the invention may be applied to a broader range of analytical reactions or other operations and varying system configurations than those described for exemplary purposes.

In some cases, the compositions, methods, and systems of the invention can be used as part of an integrated sequencing system, for example, as described in US 20120014837—Illumination of Integrated Analytical Systems, US 20120021525—Optics Collection and Detection System and Method, US 20120019828—Integrated Analytical System and Method, 61/660,776 filed Jun. 17, 2012—Arrays of Integrated Analytical Devices and Methods for Production, and US 20120085894—Substrates and Optical Systems and Methods of Use Thereof, which are incorporated herein by reference in their entirety for all purposes.

In some cases, the compositions, methods, and systems of the invention can be used in sequencing methods utilizing nanopores. Methods of nanopore sequencing are known in the art and disclosed for example in US patent application publications 2013/0327644 and 2014/0051068, which are hereby incorporated by reference in their entirety for all purposes. In some cases, the compositions, methods, and systems of the invention can be used in sequencing methods involving nanoscale electronic structures such as electrodes, capacitors, or field effect transducers (nanoFETs). NanoFETs include those having carbon nanotube gates. Such structures and their use for single molecule sequencing are described, for example, in U.S. Patent Application Publication Nos. 2015/0065353, 2016/0083789, and 2017/0037462, which are incorporated herein in their entirety for all purposes and in particular for all teachings related to structures for use in single molecule sequencing.

In certain embodiments, the compositions described herein will be provided in whole, or in part, in kit form enabling one to carry out the processes described herein. Such kits will typically comprise one or more labeling or labeled compounds of the invention, e.g., one, two, three, four, or more labeled nucleotide analogs. Such kits typically also include additional reagents, e.g., polymerase enzyme, primer sequences, buffers, and reagents that provide metal co-factors employed in the sequencing processes described herein. The kits optionally include other components for carrying out sequencing applications (or other applications involving single molecule observation or detection) in accordance with those methods described herein. In particular, such kits may include ZMW array substrates for use in observing individual molecules or reaction complexes as described herein.

In addition to the various components set forth above, the kits will typically include instructions for combining the various components in the amounts and/or ratios set forth herein, to carry out the desired processes, as also described or referenced herein, e.g., for performing sequence by incorporation reactions.

The sequencing techniques described above utilize polymerase enzymes (also referred to herein as "polymerases"). Any suitable polymerase enzyme can be used in the systems, methods, compositions, and reaction mixtures disclosed herein. Suitable polymerases include DNA dependent DNA polymerases, DNA dependent RNA polymerases, RNA dependent DNA polymerases (reverse transcriptases), and RNA dependent RNA polymerases. In certain embodiments, the polymerases used in the methods and compositions of the present invention are strand-displacing polymerases.

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a strand-displacing polymerase useful in various compositions, reaction mixtures, systems, and methods of the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Polymerases can include modifications that improve certain characteristics of the enzyme, including processivity, resistance to photodamage, and conduciveness to immobilization. In certain aspects, polymerases used in the methods and systems disclosed herein include a linker through which the polymerases (and any other molecules they are complexed with, such as template nucleic acids and optionally replication initiating moieties) can be immobilized onto a surface. Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 Polymerases For Nucleotide Analogue Incorporation by Hanzel et al. and WO 2008/051530 Polymerase Enzymes And Reagents For Enhanced Nucleic Acid Sequencing by Rank et al.), to alter branch fraction and translocation (e.g., US Pub. No. 20100075332 entitled "Engineering Polymerases And Reaction Conditions For Modified Incorporation Properties"), to increase photostability (e.g., US Pub. No. 20100093555 entitled "Enzymes Resistant to Photodamage"), and to improve surface-immobilized enzyme activities (e.g., WO 2007/075987 Active Surface Coupled Polymerases by Hanzel et al. and WO 2007/076057 Protein Engineering Strategies To Optimize Activity Of Surface Attached Proteins by Hanzel et al.). In some cases, the polymerase is modified in order to more effectively incorporate desired nucleotide analogs, e.g. analogs having four or more phosphates in their polyphosphate chain. Enzymes mutated to more readily accept nucleotide analogs having such properties are described, for example in the applications described above and in US 20120034602—Recombinant Polymerases for Improved Single Molecule Sequencing; US 20100093555—Enzymes Resistant to Photodamage; US 20110189659—Generation of Modified Polymerases for Improved Accuracy in Single Molecule Sequencing; US 20100112645—Generation of Modified Polymerases for Improved Accuracy in Single Molecule Sequencing; US 2008/0108082—Polymerase enzymes and reagents for enhanced nucleic acid sequencing; and US 20110059505—Polymerases for Nucleotide Analogue Incorporation, which are incorporated herein by reference in their entirety for all purposes.

Many polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to improve desired properties (e.g., for use in single molecule sequencing, include, e.g. Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase of use in the methods and compositions described herein is a modified Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application publications 2007-0196846, 2008-0108082, 2010-0075332, 2010-0093555, 2010-0112645, 2011-0189659, 2012-0034602, 2013-0217007, 2014-0094374, and 2014-0094375.

Many native DNA polymerases have a proof-reading exonuclease function which can yield substantial data analysis problems in processes that utilize real time observation of incorporation events as a method of identifying sequence information, e.g., single molecule sequencing applications. Even where exonuclease activity does not introduce such problems in single molecule sequencing, reduction of exonuclease activity can be desirable since it can increase accuracy (in some cases at the expense of readlength).

Accordingly, polymerases for use in the above techniques optionally include one or more mutations (e.g., substitutions, insertions, and/or deletions) relative to the parental polymerase that reduce or eliminate endogenous exonuclease activity. For example, relative to wild-type Φ29 DNA polymerase, one or more of positions N62, D12, E14, T15, H61, D66, D169, K143, Y148, and H149 is optionally mutated to reduce exonuclease activity in a recombinant Φ29 polymerase. Exemplary mutations that can reduce exonuclease activity in a recombinant Φ29 polymerase include, e.g., N62D, N62H, D12A, T15I, E14I, E14A, D66A, K143D, D145A and D169A substitutions, as well as addition of an exogenous feature at the C-terminus (e.g., a polyhistidine tag). See, e.g., US patent application publication 2014/0094375, incorporated herein by reference in its entirety for all purposes, for the sequence of wild-type Φ29 polymerase.

In some embodiments, the polymerase enzymes used in the methods and compositions of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

The polymerase enzymes of use in the present invention generally require a primer or other replication initiating moiety. While in most cases an oligonucleotide primer is used, in some cases a protein such as a terminal protein can act as a primer. In other embodiments, self-priming templates are employed. Oligonucleotide primers are generally complementary to a portion of the template nucleic acid. The primers can comprise naturally occurring RNA or DNA oligonucleotides. The primers may also be synthetic analogs. The primers may have alternative backbones as described above for the nucleic acids of the invention. The primer may also have other modifications, such as the inclusion of heteroatoms, the attachment of labels, such as dyes, or substitution with functional groups which will still allow for base pairing and for recognition by the enzyme. Primers can include tighter binding primer sequences, e.g., GC rich sequences, as well as non-natural nucleotides or nucleotide analogs, e.g., peptide nucleic acids (PNAs) or locked nucleic acids (LNAs), that can demonstrate higher affinity pairing with the template. The primer can also be selected to influence the kinetics of the polymerase reaction.

Certain methods, reaction mixtures, and compositions described herein can include template nucleic acid molecules, often as part of polymerase enzyme complexes. In general, a template nucleic acid is the molecule for which a complementary sequence is synthesized in the polymerase reaction. In some cases, the template nucleic acid is linear; in some cases, the template nucleic acid is circular. The template nucleic acid can be DNA, RNA, and/or a non-natural RNA or DNA analog. Any template nucleic acid that is suitable for replication by a polymerase enzyme can be used in the methods and systems described herein.

In some embodiments, the template nucleic acids used in methods and compositions of the present invention comprise nucleic acids obtained from a sample. The sample may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (i.e. in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.); as will be appreciated by those in the art, virtually any experimental manipulation may have been done on the samples.

In some embodiments, nucleic acid molecules are obtained from a sample and fragmented for use in methods of the invention as template nucleic acids. The fragments may be single or double stranded and can be modified in accordance with any methods known in the art and described herein. Template nucleic acids may be generated by fragmenting source nucleic acids, such as genomic DNA, using any method known in the art. In one embodiment, shear forces during lysis and extraction of genomic DNA generate fragments in a desired range. Also encompassed by the invention are methods of fragmentation utilizing restriction endonucleases. As will be appreciated, the template nucleic acids may be generated from a source nucleic acid, such as genomic DNA, by fragmentation to produce fragments of a specific size.

The template nucleic acids can be, for example, from about 10 to about 100,000 nucleotides in length, e.g., from about 10 to about 50,000 nucleotides in length, or from about 10 to about 20,000 nucleotides in length. In some embodiments, the nucleic acid templates are 10-100, 50-100, 50-300, 100-200, 200-300, 50-400, 50-600, 100-400, 200-400, 400-500, 300-600, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, 50-2000, 200-2000, 100-25000, 200-24000, 300-23000, 400-22000, 500-21000, 600-20000, 700-19000, 800-18000, 900-17000, 1000-16000, 1100-15000, 1200-14000, 1300-13000, 1400-12000, 1500-11000, 1600-10000, 1700-9000, 1800-8000, 1900-7000, 2000-6000, 2100-5000, 2200-4000, 2300-3000, 5000-20000, 10000-30000, 12000-28000, 14000-26000, 16000-24000, 18000-22000, 19000-20000, 20000-40000, or 40000-60000 nucleotides in length. In some embodiments, the nucleic acid templates are at least 5000, 10000, 15000, 20000, 25000, 30000, 40000, 50000, 60000, 70000, 80000, 90000, 100,000, 120,000, 130,000, 140,000, or 150,000 nucleotides in length. In some embodiments, the nucleic acid templates are part of polymerase-template complexes. In some embodiments, the nucleic acid templates are themselves further hybridized to primers.

In some cases, the template may be a linear single or double stranded nucleic acid. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, and alternate functional circular constructs are also described in US Pat. App. Pub. No. 20090298075, the full disclosures of each of which are incorporated herein by reference in their entirety for all purposes and in particular for all teachings related to template nucleic acid constructs. Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

In some aspects, the template nucleic acid used in the compositions of the present invention includes: a double stranded nucleic acid segment having a first and second end; a first hairpin oligonucleotide connecting each strand of the single template nucleic acid at the first end; and a second hairpin oligonucleotide connecting each strand of the single template nucleic acid at the second end. In some embodiments, the first hairpin and second hairpin oligonucleotide are identical. In other embodiments, the first hairpin and second hairpin oligonucleotides are not identical—in other words, the template nucleic acid, despite being an alternate circular construct, is nevertheless asymmetrical. In some embodiments, the first hairpin oligonucleotide includes a primer binding site whereas the second hairpin oligonucleotide includes a capture adapter (or vice versa). The capture adapter is generally of a sequence that can be used to enrich a population for the hairpins of choice—for example, in some embodiments, the capture adapter comprises a polyA sequence, thereby allowing capture using beads or column chromatography utilizing polyT sequences. In other embodiments, the capture adapter comprises at least one methoxy residue. In some embodiments, the capture adapter is complementary to an oligonucleotide attached to a bead, which can be a magnetic bead that can be used to enrich a population for template nucleic acids containing the capture adapter. In some embodiments in which the population of templates includes templates with different adapters or in which each template comprises a different adapter at each end, different beads can be used which contain oligonucleotides complementary to the different adapters. Thus, for templates with two different adapters, two different beads can be used. For populations containing a plurality of different adapters, a concomitant number of different types of beads can be used that are directed to those adapters. In other embodiments, the same bead can contain different oligonucleotides complementary to the different adapters in the population of templates, such that the same bead can capture different adapters (and their associated templates). In some embodiments, the first or second hairpin comprises a self-primed adapter sequence in which the primer is part of the adapter. In such embodiments, an additional oligonucleotide primer is not needed to allow a polymerase molecule to begin replicating the template. In some embodiments, the nucleic acid template contains only a single hairpin at one end or the other.

The practice of the present invention can employ, unless otherwise indicated, conventional techniques and descriptions of organic chemistry, polymer technology, molecular biology (including recombinant techniques), cell biology, biochemistry, immunology, and the like which are within the skill of the art. Such conventional techniques include polymer array synthesis, hybridization, ligation, phage display, and detection of hybridization using a label. Specific illustrations of suitable techniques can be had by reference to the examples herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Current Protocols in Molecular Biology, F. M. Ausubel et al., eds., Current Protocols, a joint venture between Greene Publishing Associates, Inc. and John Wiley & Sons, Inc., (supplemented through 2017), Stryer, L. (1995) Biochemistry (4th Ed.) Freeman, N.Y., Gait, "Oligonucleotide Synthesis: A Practical Approach" 1984, IRL Press, London, Nelson and Cox (2000), Lehninger, Principles of Biochemistry 3' Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

A variety of protein isolation and detection methods are known and can be used to isolate polymerases, biotin-binding proteins or other proteins suitable for use as protein cores in compositions of the invention, e.g., from recombinant cultures of cells expressing recombinant proteins. Such techniques can similarly be employed to isolate multimeric biotin-binding proteins from monomers or to isolate particular multimeric forms (e.g., a desired tetramer including one tagged subunit and three untagged subunits from tetramers including more or less than one tagged subunit). Such techniques can also be employed to isolate desired products (e.g., a desired product including two SA-1Tag tetramers and one SA-2Catcher tetramer as shown in FIG. 1B from undesired products including only one SA-1Tag tetramer and one SA-2Catcher tetramer). A variety of protein isolation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3$^{rd}$ Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1: Production of Modular Multi-Amplitude Nucleotide Analogs

Production of two modular multi-amplitude nucleotide analogs is schematically illustrated in FIGS. 7A-7B.

Streptavidin, SpyTag fused to streptavidin, and Spy-Catcher fused to streptavidin are expressed and purified basically as described in Sano and Cantor (1990) "Expression of a cloned streptavidin gene in *Escherichia coli*" Proc Natl Acad Sci USA 87:142-6 and Fairhead et al. (2014) "SpyAvidin hubs enable precise and ultrastable orthogonal nanoassembly" J. Am. Chem. Soc. 136: 12355-12363. Mixed tetramers including either three streptavidin subunits and one subunit having SpyTag fused to streptavidin (SA-1Tag) or three streptavidin subunits and one subunit having SpyCatcher fused to streptavidin (SA-1Catcher) are formed and isolated basically as described, e.g., in Fairhead et al. (2014) supra.

A modular analog including two C nucleotide components and two copies of a dye component is produced as schematically illustrated in FIG. 7A.

Figure 8:
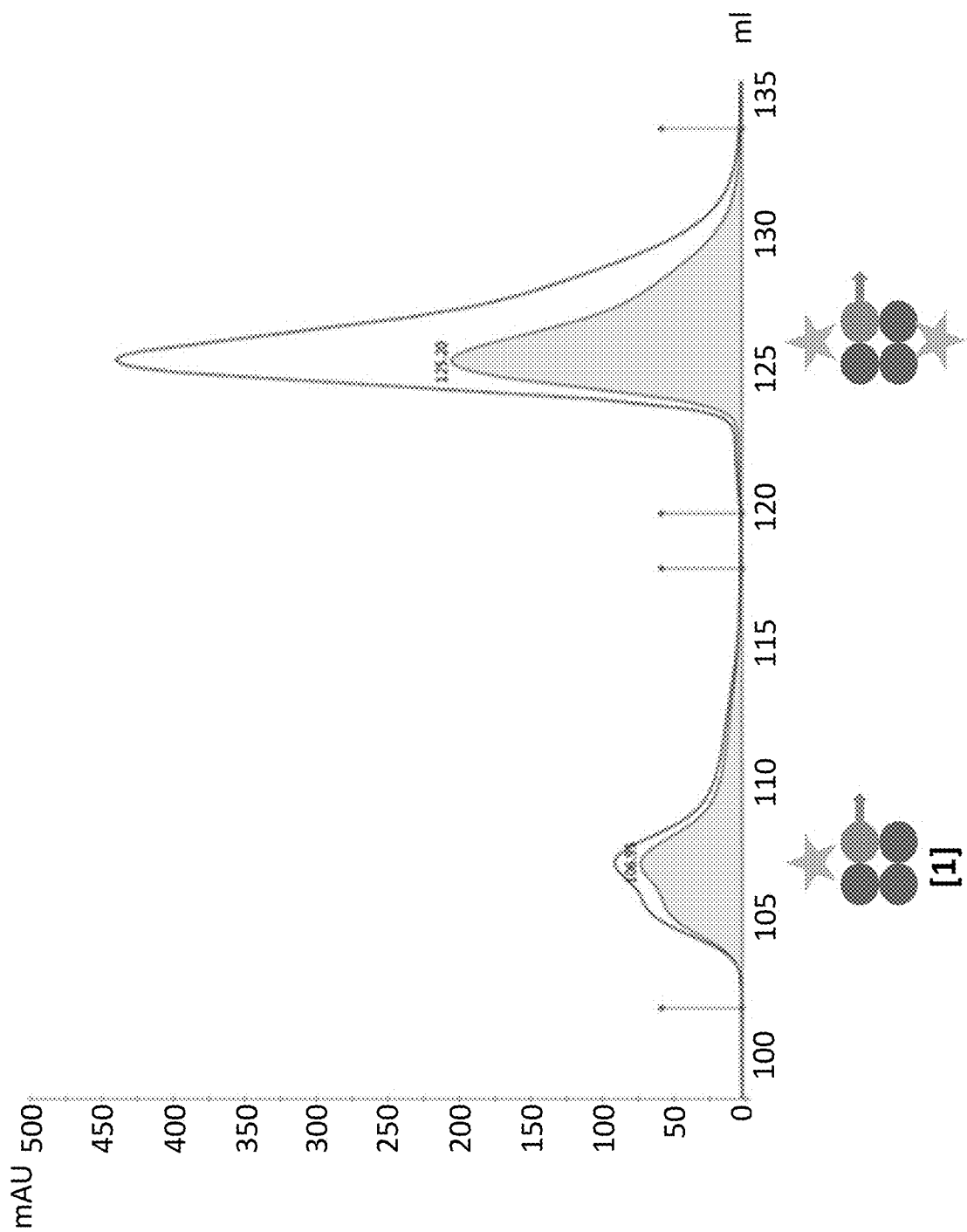
FIG. 8 shows a chromatogram illustrating purification of an intermediate used in production of a modular analog.

A concentrated stock of the SA-1Tag heterotetramer is prepared (50-170 nmol of tetrameric SA). 30 nmol-60 nmol of bis-biotinylated dye component is diluted in 4 ml of Buffer A (5 mM TrisCl, pH 7.4, 20% Acetonitrile). Note that the heterotetramer is preferably in excess to the dye component. The diluted dye component solution is added to the streptavidin solution in 25 µL increments as the solution is being stirred. The sample is cleared by centrifugation at 4° C. for 20 min at 15000 rpm. The supernatant is loaded to the 5 ml sample loop of FPLC (fast protein liquid chromatography system). Purification is performed on HITRAP Q HP Q SEPHAROSE anion exchange column (GE Healthcare Life Sciences) with Buffer A and Buffer B (5 mM TrisCl, pH 7.4, 1.5M NaCl, 20% Acetonitrile). Eluted fractions are collected, and the buffer is exchanged to 5 mM TrisCl, pH 7.4. The elution profile is shown in FIG. 8. The SA-1Tag heterotetramer is collected in the flow-through fraction. The first elution peak is the desired SA-1Tag bearing one bis-biotinylated dye component (intermediate [1]), and the second elution peak is SA-1Tag with two bound dye components.

Where X is the nmol of intermediate [1], 1.2X nmol of bis-biotinylated C nucleotide component is diluted in 1 ml of Buffer A and added to X nmol of intermediate [1] that has been diluted to 4 ml of Buffer A. Excess nucleotide component is removed using an Amicon 30K filter. The retentate is re-diluted into 5 ml of Buffer A and then loaded to the 5 ml sample loop of FPLC. Anion exchange chromatography is performed as described above. The elution peak containing intermediate [2] (SA-1Tag with a bound nucleotide component and a bound dye component) is collected, and the buffer is exchanged to 5 mM TrisCl, pH 7.4. (The order of dye and nucleotide component binding can be reversed; yield can be increased by binding the nucleotide component first and then the dye component.)

Intermediate [3], SA1-Catcher with a bound dye component, is prepared basically as described for intermediate [1] above, except that free SA1-Catcher is observed in an early peak rather than in the flow-through. Intermediate [4], SA1-Catcher with one dye component and one C nucleotide component, is prepared from intermediate [3] basically as described above for intermediate [2].

Figure 9:
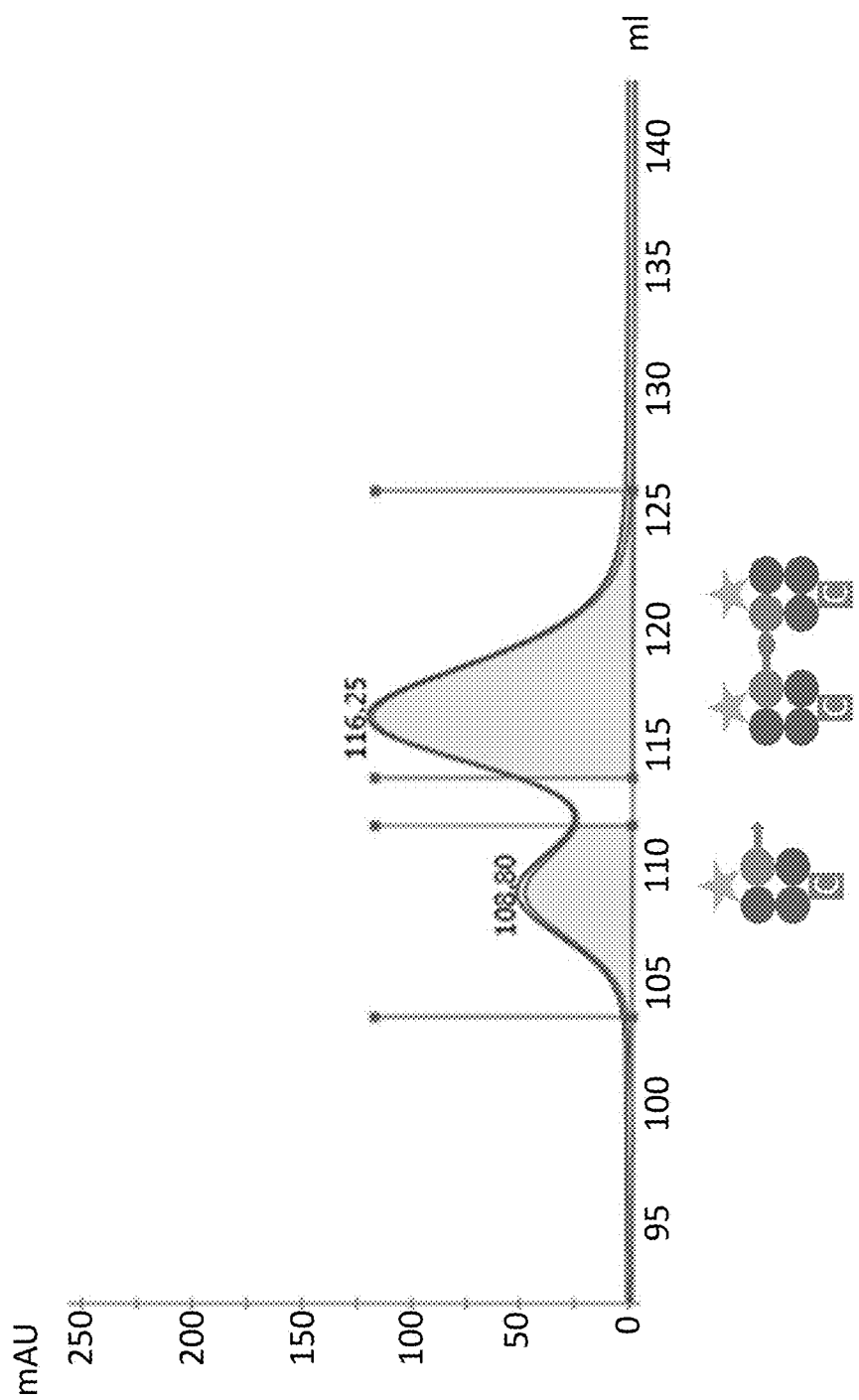
FIG. 9 shows a chromatogram illustrating isolation of a modular analog.

Intermediates [2] and [4] are conjugated to produce the desired analog that contains two streptavidin cores, two dye components, and two C nucleotide components. Intermediates [2] and [4] are prepared to at least 10 µM. 1.3X of intermediate [2] and 1X of intermediate [4] are mixed and incubated in the dark at room temperature for 2 hours. The mixture is then loaded to the 5 ml sample loop of FPLC (fast protein liquid chromatography system) and anion exchange chromatography is performed basically as described above. The eluted fraction containing the analog is collected, and the buffer is exchanged to 5 mM TrisCl, pH 7.4. The elution profile is shown in FIG. 9. Unreacted intermediate [2] elutes first, followed by the desired analog.

Another analog, this one including an A nucleotide component and one copy of the same dye component, is produced as schematically illustrated in FIG. 7B. Beginning with a concentrated solution of tetrameric streptavidin, the desired analog is produced essentially as described above for intermediates [2] and [4].

A corresponding pair of analogs, including either two copies of a T nucleotide component and two copies of a second dye component (different from that used in the A and C analogs) or one copy of a G nucleotide component and one copy of the second dye component, are also produced. The set of four nucleotides is used in single molecule DNA sequencing reactions on a SEQUEL sequencing system from Pacific Biosciences of California.

Example 2: Exemplary Constructs

Exemplary protein sequences suitable for use in the methods and compositions of the invention are presented in Table 1. A core streptavidin is presented as SEQ ID NO:1 (full length streptavidin also includes N- and C-terminal sequences that are typically removed by processing, yielding a shorter core sequence with higher biotin binding affinity; an N-terminal methionine has been added for expression). SpyTag fused to streptavidin is presented as SEQ ID NO:2, and SpyCatcher fused to streptavidin is presented as SEQ ID NO:3. The N-terminal histidine tag on the fusion constructs can facilitate purification of specific heterotetramers; the His tag can then be removed by digestion with thrombin to ensure that the tag does not interfere with subsequent applications (e.g., where the streptavidin constructs are incorporated into nucleotide analogs for use in single molecule sequencing). The thrombin recognition site employed is LVPRGS (SEQ ID NO:4). Glycine-serine linkers are included between domains (GGGSGGGSGGGS, SEQ ID NO:5 and GGGSGGGS, SEQ ID NO:6); it will be evident that any of a variety of other linkers well known in the art can be employed, or the domains can be fused without a linker. It will also be evident that any of a variety of related constructs can also be employed, e.g., including different versions of the SpyTag or SpyCatcher sequences, mutated forms of streptavidin, and/or different (or no) tags, linkers, protease sites, and the like. Similarly, SnoopTag/Snoop-Catcher or other similar systems can be employed, as can other biotin-binding proteins.

TABLE 1

| Exemplary streptavidin sequences. | |
|---|---|
| streptavidin SEQ ID NO: 1 | MGEAGITGTWYNQLGSTFIVTAGADGALTGTYESA VGNAESRYVLTGRYDSAPATDGSGTALGWTVAWK NNYRNAHSATTWSGQYVGGAEARINTQWLLTSGTT EANAWKSTLVGHDTFTKVKPSAAS |
| streptavidin-SpyTag fusion- His6.LVPRGS. Streptavidin. GGGSGGGSGGGS.SpyTag SEQ ID NO: 2 | MHHHHHHLVPRGSGEAGITGTWYNQLGSTFIVTAG ADGALTGTYESAVGNAESRYVLTGRYDSAPATDGS GTALGWTVAWKNNYRNAHSATTWSGQYVGGAEA RINTQWLLTSGTTEANAWKSTLVGHDTFTKVKPSA ASGGGSGGGSGGGSAHIVMVDAYKPTK |
| streptavidin-SpyCatcher fusion- His6.LVPRGS. Streptavidin. GGGSGGGS.SpyCatcher SEQ ID NO: 3 | MHHHHHHLVPRGSEAGITGTWYNQLGSTFIVTAGA DGALTGTYESAVGNAESRYVLTGRYDSAPATDGSG TALGWTVAWKNNYRNAHSATTWSGQYVGGAEARI NTQWLLTSGTTEANAWKSTLVGHDTFTKVKPSAAS GGGSGGGSDYDIPTTENLYFQGAMVDTLSGLSSEQG QSGDMTIEEDSATHIKFSKRDEDGKELAGATMELRD SSGKTISTWISDGQVKDFYLYPGKYTFVETAAPDGY EVATAITFTVNEQGQVTVNGKATKGDAHI |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What it claimed is:

1. A set of dye-labeled nucleotide analogs, the set comprising:

a first labeled nucleotide analog comprising i) one or more tetravalent biotin-binding proteins, ii) one or more first nucleotide components bound to the one or more tetravalent biotin-binding proteins, and iii) one or more dye components bound to the one or more tetravalent biotin-binding proteins, each dye component comprising one or more dye moieties; and a second labeled nucleotide analog comprising i) two or more covalently linked tetravalent biotin-binding proteins, ii) one or more second nucleotide components bound to the two or more tetravalent biotin-binding proteins, and iii) two or more dye components bound to the two or more tetravalent biotin-binding proteins, each dye component comprising one or more dye moieties;

wherein the total number of dye moieties in the second labeled nucleotide analog is greater than that in the first labeled nucleotide analog.

2. The set of claim 1, wherein, in the first labeled nucleotide analog, each of the one or more first nucleotide components and the one or more dye components is bound to the one or more tetravalent biotin-binding proteins through a biotin moiety; and wherein, in the second labeled nucleotide analog, each of the one or more second nucleotide components and the two or more dye components is bound to the two or more tetravalent biotin-binding proteins through a biotin moiety.

3. The set of claim 1, wherein, in the first labeled nucleotide analog, each of the one or more first nucleotide components and the one or more dye components comprises a bis-biotin moiety bound to two biotin binding sites on the one or more tetravalent biotin-binding proteins; and wherein, in the second labeled nucleotide analog, each of the one or more second nucleotide components and the two or more dye components comprises a bis-biotin moiety bound to two biotin binding sites on the two or more tetravalent biotin-binding proteins.

4. The set of claim 1, comprising a third labeled nucleotide analog comprising i) two or more covalently linked tetravalent biotin-binding proteins, ii) one or more third nucleotide components bound to the two or more tetravalent biotin-binding proteins, and iii) three or more dye components bound to the two or more tetravalent biotin-binding proteins, each dye component comprising one or more dye moieties;
wherein the total number of dye moieties in the third labeled nucleotide analog is greater than that in the second labeled nucleotide analog.

5. The set of claim 4, comprising a fourth labeled nucleotide analog comprising i) three or more covalently linked tetravalent biotin-binding proteins, ii) one or more fourth nucleotide components bound to the three or more tetravalent biotin-binding proteins, and iii) four or more dye components bound to the three or more tetravalent biotin-binding proteins, each dye component comprising one or more dye moieties;
wherein the total number of dye moieties in the fourth labeled nucleotide analog is greater than that in the third labeled nucleotide analog.

6. The set of claim 5, wherein the first labeled nucleotide analog comprises one dye component, the second labeled nucleotide analog comprises two dye components, the third labeled nucleotide analog comprises three dye components, and the fourth labeled nucleotide analog comprises four dye components.

7. The set of claim 6, wherein each dye component comprises a single, identical dye moiety.

8. The set of claim 6, wherein the first labeled nucleotide analog comprises one tetravalent biotin-binding protein and one first nucleotide component, the second labeled nucleotide analog comprises two tetravalent biotin-binding proteins and two second nucleotide components, the third labeled nucleotide analog comprises two tetravalent biotin-binding proteins and one third nucleotide component, and the fourth labeled nucleotide analog comprises three tetravalent biotin-binding proteins and two fourth nucleotide components.

9. The set of claim 1, wherein the dye components in the first and second labeled nucleotide analogs are identical.

10. The set of claim 1, wherein the dye moieties are fluorescent dye moieties.

11. The set of claim 1, wherein the first nucleotide component comprises at least one phospholinked first nucleotide moiety, wherein the second nucleotide component comprises at least one phospholinked second nucleotide moiety, and wherein the first and second nucleotide moieties comprise different nucleobases.

12. The set of claim 1, wherein the first labeled nucleotide analog comprises two or more covalently linked tetravalent biotin-binding proteins and two or more first nucleotide components bound to the two or more tetravalent biotin-binding proteins.

13. The set of claim 1, wherein the one or more tetravalent biotin-binding proteins in the first labeled nucleotide analog and the two or more tetravalent biotin-binding proteins in the second labeled nucleotide analog comprise streptavidin or traptavidin.

14. The set of claim 1, wherein the second labeled nucleotide analog comprises two or more tetravalent biotin-binding proteins covalently linked by at least one isopeptide bond.

15. The set of claim 1, wherein the second labeled nucleotide analog comprises two or more tetravalent biotin-binding proteins covalently linked through at least one bifunctional or multifunctional crosslinker.

16. A reaction mixture for sequencing a nucleic acid template, the mixture comprising
a polymerase enzyme complex comprising a polymerase enzyme, a template nucleic acid, and optionally a primer hybridized to the template nucleic acid, wherein the polymerase enzyme complex is immobilized on a surface; and
sequencing reagents in contact with the surface, comprising reagents for carrying out nucleic acid synthesis including the set of dye-labeled nucleotide analogs of claim 1.

17. A method for sequencing a nucleic acid template, the method comprising
providing a polymerase enzyme complex comprising a polymerase enzyme, a template nucleic acid, and optionally a primer hybridized to the template nucleic acid, wherein the polymerase enzyme complex is immobilized on a surface;
adding sequencing reagents in contact with the surface comprising reagents for carrying out nucleic acid synthesis including the set of dye-labeled nucleotide analogs of claim 1; and
determining the sequential addition of nucleotides to a nucleic acid strand complementary to a strand of the template nucleic acid by observing the interaction of the dye-labeled nucleotide analogs with the polymerase enzyme complex.

18. A system for sequencing nucleic acids, the system comprising
a chip comprising a plurality of polymerase enzyme complexes bound to its surface, each polymerase enzyme complex individually optically resolvable, each polymerase enzyme complex comprising a polymerase enzyme, a template nucleic acid, and optionally a primer hybridized to the template nucleic acid, and sequencing reagents in contact with the surface comprising reagents for carrying out nucleic acid synthesis including the set of dye-labeled nucleotide analogs of claim 1;
an illumination system for illuminating the polymerase enzyme complexes;
an optical detection system for detecting fluorescence from the labeled nucleotide analogs while they are interacting with the polymerase enzyme complexes; and
a computer for analyzing the signals detected by the detection system to determine the sequential addition of nucleotides to a nucleic acid strand complementary to a strand of the template nucleic acid.

* * * * *

SEQUENCE LISTING

```
<160> NUMBER OF SEQ ID NOS: 6

<210> SEQ ID NO 1
<211> LENGTH: 128
<212> TYPE: PRT
<213> ORGANISM: Streptomyces avidinii

<400> SEQUENCE: 1

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125

<210> SEQ ID NO 2
<211> LENGTH: 165
<212> TYPE: PRT
<213> ORGANISM: Artificial Sequence
<220> FEATURE:
<223> OTHER INFORMATION: fusion protein including streptavidin and
      SpyTag
```

<400> SEQUENCE: 2

```
Met His His His His His Leu Val Pro Arg Gly Ser Gly Glu Ala
1               5                   10                  15

Gly Ile Thr Gly Thr Trp Tyr Asn Gln Leu Gly Ser Thr Phe Ile Val
                20                  25                  30

Thr Ala Gly Ala Asp Gly Ala Leu Thr Gly Thr Tyr Glu Ser Ala Val
            35                  40                  45

Gly Asn Ala Glu Ser Arg Tyr Val Leu Thr Gly Arg Tyr Asp Ser Ala
    50                  55                  60

Pro Ala Thr Asp Gly Ser Gly Thr Ala Leu Gly Trp Thr Val Ala Trp
65                  70                  75                  80

Lys Asn Asn Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Ala Asn Ala Trp Lys Ser Thr Leu Val Gly His
            115                 120                 125

Asp Thr Phe Thr Lys Val Lys Pro Ser Ala Ala Ser Gly Gly Gly Ser
130                 135                 140

Gly Gly Gly Ser Gly Gly Ser Ala His Ile Val Met Val Asp Ala
145                 150                 155                 160

Tyr Lys Pro Thr Lys
                165
```

<210> SEQ ID NO 3
<211> LENGTH: 276
<212> TYPE: PRT
<213> ORGANISM: Artificial Sequence
<220> FEATURE:
<223> OTHER INFORMATION: fusion protein including streptavidin and SpyCatcher

<400> SEQUENCE: 3

```
Met His His His His His Leu Val Pro Arg Gly Ser Glu Ala Gly
1               5                   10                  15

Ile Thr Gly Thr Trp Tyr Asn Gln Leu Gly Ser Thr Phe Ile Val Thr
                20                  25                  30

Ala Gly Ala Asp Gly Ala Leu Thr Gly Thr Tyr Glu Ser Ala Val Gly
            35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Gly Gly Gly Ser Gly
    130                 135                 140

Gly Gly Ser Asp Tyr Asp Ile Pro Thr Thr Glu Asn Leu Tyr Phe Gln
145                 150                 155                 160

Gly Ala Met Val Asp Thr Leu Ser Gly Leu Ser Ser Glu Gln Gly Gln
                165                 170                 175
```

```
Ser Gly Asp Met Thr Ile Glu Glu Asp Ser Ala Thr His Ile Lys Phe
            180                 185                 190

Ser Lys Arg Asp Glu Asp Gly Lys Glu Leu Ala Gly Ala Thr Met Glu
            195                 200                 205

Leu Arg Asp Ser Ser Gly Lys Thr Ile Ser Thr Trp Ile Ser Asp Gly
            210                 215                 220

Gln Val Lys Asp Phe Tyr Leu Tyr Pro Gly Lys Tyr Thr Phe Val Glu
225                 230                 235                 240

Thr Ala Ala Pro Asp Gly Tyr Glu Val Ala Thr Ala Ile Thr Phe Thr
                245                 250                 255

Val Asn Glu Gln Gly Gln Val Thr Val Asn Gly Lys Ala Thr Lys Gly
            260                 265                 270

Asp Ala His Ile
        275

<210> SEQ ID NO 4
<211> LENGTH: 6
<212> TYPE: PRT
<213> ORGANISM: Artificial Sequence
<220> FEATURE:
<223> OTHER INFORMATION: oligopeptide thrombin recognition site

<400> SEQUENCE: 4

Leu Val Pro Arg Gly Ser
1               5

<210> SEQ ID NO 5
<211> LENGTH: 12
<212> TYPE: PRT
<213> ORGANISM: Artificial Sequence
<220> FEATURE:
<223> OTHER INFORMATION: oligopeptide glycine-serine linker

<400> SEQUENCE: 5

Gly Gly Gly Ser Gly Gly Gly Ser Gly Gly Gly Ser
1               5                   10

<210> SEQ ID NO 6
<211> LENGTH: 8
<212> TYPE: PRT
<213> ORGANISM: Artificial Sequence
<220> FEATURE:
<223> OTHER INFORMATION: oligopeptide glycine-serine linker

<400> SEQUENCE: 6

Gly Gly Gly Ser Gly Gly Gly Ser
1               5
```